United States Patent [19]

Srinivasan et al.

[11] Patent Number: 5,436,352
[45] Date of Patent: Jul. 25, 1995

[54] METAL RADIONUCLIDE CHELATING COMPOUNDS FOR IMPROVED CHELATION KINETICS

[75] Inventors: Ananthachari Srinivasan, Kirkland; Alan R. Fritzberg, Edmonds; David S. Jones, Seattle, all of Wash.

[73] Assignee: NeoRx Corporation, Seattle, Wash.

[21] Appl. No.: 804,123

[22] Filed: Dec. 6, 1991

Related U.S. Application Data

[62] Division of Ser. No. 589,449, Sep. 27, 1990, Pat. No. 5,075,099, which is a division of Ser. No. 201,134, May 31, 1988, Pat. No. 4,988,496.

[51] Int. Cl.⁶ .............. C07D 207/46; C07D 315/00; C07C 233/01; C07C 67/00
[52] U.S. Cl. .................... 548/542; 549/415; 549/419; 549/472; 549/479; 564/154; 558/232; 558/251; 558/256
[58] Field of Search ............ 548/546, 547, 544, 542; 564/336, 340, 153, 154, 367, 372; 549/472, 415, 479, 419, 426; 558/232, 251, 256

[56] References Cited

U.S. PATENT DOCUMENTS

| | | | |
|---|---|---|---|
| 4,914,241 | 4/1990 | Hesse et al. | 564/485 |
| 4,987,130 | 1/1991 | Tsushima et al. | 514/210 |
| 5,196,550 | 3/1993 | Long, III et al. | 548/548 |

FOREIGN PATENT DOCUMENTS 188256 7/1986 European Pat. Off. .

OTHER PUBLICATIONS

Greene, *Protective Groups in Organic Synthesis*, Chapter 6, pp. 914–196, 1981.
Yano et al., "4-Substituted 1,2-dithiolane derivatives," Jap. Pat. No. 61,103,880 (May 22, 1986) as abstracted in CA105:208855.
Bal et al., Rocz. Chem. 50(5):961–6 as abstracted in CA86:29452, 1976.

*Primary Examiner*—Gary Geist
*Assistant Examiner*—Lara E. Chapman
*Attorney, Agent, or Firm*—Seed and Berry

[57] ABSTRACT

The present invention provides metal chelating compounds, to chelates and chelate-targeting agent conjugates formed from the chelating compounds, and to methods for making and using these compositions. The chelating compounds incorporate two nitrogen atoms and three sulfur atoms ("$N_2S_3$"), two nitrogen atoms and four sulfur atoms ("$N_2S_4$"), or three nitrogen atoms and three sulfur atoms ("$N_3S_3$"). Metals, and metal oxides, capable of being chelated by the compounds include those that are radionuclides, such as $^{99m}Tc$ and $^{186/188}Re$.

The targeting agent portion of the chelate-targeting agent conjugates provided includes antibodies, peptides, hormones, enzymes and biological response modifiers. Methods for making the conjugates are provided and encompass the addition of a metal, or metal oxide, to a chelating compound prior to attachment to a targeting agent as well as subsequent to the attachment.

Another aspect of the invention provides kits for producing chelate-targeting agent conjugates for radiopharmaceutical use.

An additional aspect of the invention provides methods for using the chelate-targeting agent conjugates for diagnostic and therapeutic purposes, such as detection of a target site and delivery of a radionuclide to the site, respectively.

5 Claims, No Drawings

METAL RADIONUCLIDE CHELATING COMPOUNDS FOR IMPROVED CHELATION KINETICS

CROSS REFERENCE TO RELATED APPLICATION

This application is a division of Ser. No. 07/589,449, filed Sep. 27, 1990, issued Dec. 24, 1991, as U.S. Pat. No. 5,075,099, which is a division of Ser. No. 07/201,134, filed May 31, 1988, issued Jan. 29, 1991, as U.S. Pat. No. 4,988,496.

TECHNICAL FIELD

The present invention relates generally to metal chelating compounds, to chelates and chetate-targeting agent conjugates formed from the chelating compounds, and to methods for making and using these compositions. This invention is more particularly related to chelate-targeting agent conjugates in which the metal is a radionuclide and to methods employing the conjugates for diagnostic and therapeutic purposes.

BACKGROUND OF THE INVENTION

Radiolabeled chelating compounds are useful medical agents. For example, radiolabeled ethylenediamine tetraacetic acid (EDTA), diethylenetetramine-pentaacetate (DTPA) and o-iodohippurate (OIH) have been reported to be useful in evaluating renal functions (Klingensmith et al., *J. Nucl. Med.* 29: 377, 1982). Similarly, Kasina et al., *J. Med. Chem.* 29:1933 (1986), report promising renal pharmaceuticals that are technetium ($^{99m}$Tc) chelates of diamide-dimercaptides (N$_2$S$_2$). Other medically useful chelates that have been reported include: tartrate and orthophosphate, Molinksi et al., U.S. Pat. No. 3,987,157; propylene amine oxime, Troutner et al., U.S. Pat. No. 4,615,876; poly-hydroxy-carboxylic acids, Adler et al., U.S. Pat. No. 4,615,876; poly-hydroxy-carboxylic acids, Adler et al., U.S. Pat. No. 4,027,005; organo-trisubstituted trivalent phophorus compounds, Dean et al., U.S. Pat. No. 4,582,700; bis(thiosemicarbazone), Vedee et al., U.S. Pat. No. 4,564,472; mercaptoacetylglycylglycylglycine (MAG$_3$) Fritzberg et al., *J. Nucl. Med.* 27: 111-116, 1986; mercaptocarboxylic acids, Winchell et al., U.S. Pat. No. 4,233,285; homocysteine and cysteinamide derivatives, Byrne et al., U.S. Pat. No. 4,571,430; metallothionine, Tolman, European application 4-10-84 0 137 457 AZ; isonitrile, Jones et al., U.S. Pat. No. 4,452,774; and imidodiphosphonate, Subramaniam et al., U.S. Pat. No. 3,974,268.

Chelating compounds are useful both as therapeutic and diagnostic agents. They are investigated for the purpose of stably linking the radionuclides to target-specific biological molecules such as antibodies and antibody fragments. Diagnostic imaging of specific target tissue in vivo with a radiometal-chelate-antibody conjugate was reported by Khaw et al., *Science* 209:295, 1980. Similarly, the therapeutic use of radiometal-chelate-antibody conjugates to treat cellular disorders is referred to by Gansow et al., U.S. Pat. No. 4,454,106.

Difficulties associated with the known chelating compounds have limited their usefulness. For example, the rate of chelation of diamide-dimercaptide (N$_2$S$_2$) ligands is relatively low despite the high stability of the Tc and Re complexes formed. An alternative approach, direct attachment of radionuclides to reduced proteins, also results in the formation of a complex in which metal is bound to thiolate and other groups such as amide, amine and carboxylate. However, stability problems have often limited their use in diagnostic and therapeutic applications involving antibody and antibody fragments. The stability problems can be attributed, in part, to the large metal chelate ring sizes required to attain desired donor atom to metal ratios.

Thus, there is a need in the art for metal chelating compounds which are capable of both rapidly complexing a metal and forming a stable chelate. The present invention fulfills this need and further provides other related advantages.

SUMMARY OF THE INVENTION

Briefly stated, the present invention, in one aspect, provides a compound having the formula (I):

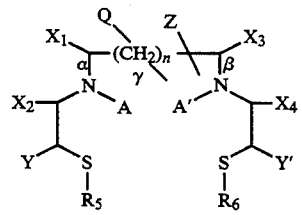

wherein:

$X_1$ and $X_2$ are H or =O, but both are not =O;

$X_3$ and $X_4$ are H or =O, but both are not =O;

A is H, alkyl group of C$_6$ or less, —CH$_2$—CH$_2$—S—R$_1$ or —CO—CH$_2$—S—R$_1$, with the proviso that when $X_1$ or $X_2$ is =O, A is H;

A′ is H, alkyl group of C$_6$ or less, 3—CH$_2$—CH$_2$—S—R$_2$ or —CO—CH$_2$—S—R$_2$, with the proviso that when $X_3$ or $X_4$ is =O, A′ is H;

Y is
(a) —CH$_2$—S—R$_3$, or H, when A is H or an alkyl group of C$_6$ or less and A′ is H or an alkyl group of C$_6$ or less, or
(b) H;

Y′ is
(a) —CH$_2$—S—R$_4$, or H, when A is H or an alkyl group of C$_6$ or less and A′ is H or an alkyl group of C$_6$ or less, with the proviso that Y and Y′ are not both H, or
(b) H;

R$_1$, R$_2$, R$_3$, R$_4$, R$_5$, and R$_6$ are independently selected from sulfur protecting groups;

Q is H or a polar group to increase the hydrophilicity of the compound;

n is 0 to 2; and

Z is —(W)$_m$—R′ where W is —CH$_2$—, —CH$_2$—O—, —CH$_2$—CO—, or combination thereof, m is 0 to 5, and R′ is a chemically reactive group, with the provisos that when Z is attached to the carbon designated α there is either no $X_1$ or no Q at α, that when Z is attached to the carbon designated β there is either no $X_3$ or no Q at β, that when $X_1$ is =O there is no Z at α, and that when $X_3$ is =O there is no Z at β.

Chelates, chelate-targeting agent conjugates, and methods for producing them from compound I are provided. The targeting agent is attached via the reactive group R′, to the chelating compound or the chelate.

In another aspect, the invention provides a compound having the formula (II):

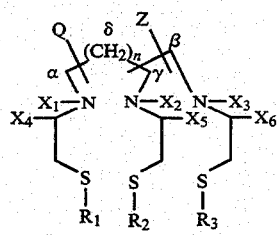

wherein:
$R_1$, $R_2$, and $R_3$ are independently selected from sulfur protecting groups;
$X_1$ and $X_2$ are independently selected from H and an alkyl group of $C_6$ or less;
$X_3$ is H, an alkyl group of $C_6$ or less, or Z;
$X_4$, $X_5$, and $X_6$ are independently selected from H and =O, with the provisos that $X_4$ is H when $X_1$ is an alkyl group, that $X_5$ is H when $X_2$ is an alkyl group, and that $X_6$ is H when $X_3$ is an alkyl group or Z;
Q is H or a polar group to increase the hydrophilicity of the compound;
n is 0 to 4; and
Z is —(W)$_m$—R', where W is —CH$_2$—, —CH$_2$—O—, —CH$_2$—CO—, or combinations thereof, m is 0 to 5, and R' is a chemically reactive group.

Chelates, chelate-targeting agent conjugates, and methods for producing them from compound II are provided. The targeting agent is attached via the reactive group, R', to the chelating compound or the chelate.

Another aspect of the present invention provides kits for producing chelate-targeting agent conjugates for radiopharmaceutical use. A metal radionuclide may be added to a chelating compound of formula I or II, either before or after the chelating compound is attached to a targeting agent.

Yet another aspect of the invention provides methods for using the chelate-targeting agent conjugates described above for diagnostic and therapeutic purposes. A diagnostic method is described for detecting the presence or absence of a target site within a mammalian host. This method comprises the steps of administering to a mammal a diagnostically effective dose of the chelate-targeting agent conjugate containing a metal radionuclide, such as $^{99m}$Tc, and detecting the biodistribution of the radionuclide. A therapeutic method is described for delivering a radionuclide, such as $^{186}$Re or $^{188}$Re, to a target site within a mammalian host. This method comprises the step of administering to a mammal a therapeutically effective dose of the chelate-targeting agent conjugate.

Other aspects of the invention will become evident upon reference to the following detailed description.

DETAILED DESCRIPTION OF THE INVENTION

Prior to setting forth the invention, it may be helpful to an understanding thereof to set forth definitions of certain terms to be used hereinafter.

Targeting agent—is any molecule that has the capacity to bind to a defined population of cells.

Protein—as used herein, includes proteins, polypeptides, and peptides; and may be an intact molecule, a fragment thereof, or a functional equivalent thereof; and may be genetically engineered; an example is an antibody.

Antibody—as used herein, includes both polyclonal and monoclonal antibodies; and may be an intact molecule, a fragment thereof, or a functional equivalent thereof; and may be genetically engineered; examples of antibody fragments include F(ab')$_2$, Fab', Fab and Fv.

As noted above, the present invention provides compounds of two general formulae that are capable of chelating metals. An advantage of these compounds is that they are capable of rapidly complexing a metal as well as forming a stable chelate. The presence of nitrogen (N) atoms within the chelating compound accelerates complex formation with a metal. This acceleration is due, in part, to the fact that a metal, e.g., Tc, is a soft acid and N, in the form of an amine or amide, is a base. Amines provide a greater increase in chelation rates than amides. The presence of sulfur (S) atoms within the chelating compound, in addition to providing for increased rates of complexation, contribute to the stability of the resulting chelate. Thus, the compounds of the present invention represent a combination of desirable kinetic properties for the formation of a complex with a metal and desirable thermodynamic properties for the retention of the metal. Accordingly, attachment of radionuclides to targeting agent-chelate conjugates formed from the compounds of the present invention which possess increased —S—(thiolate) groups situated at an appropriate distance alleviates the stability and kinetic problems encountered in both the direct metallation reaction of proteins and protein-chelate conjugates formed from the known chelating compounds.

Compound I has the following formula:

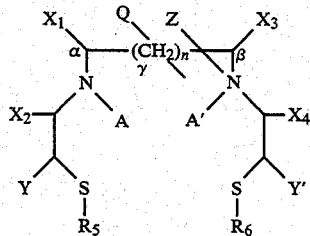

Examples of specific embodiments of the elements of compound I include the following.

$X_1$ and $X_2$ may be H or an oxy group (=O), but both are not =O. Likewise, $X_3$ and $X_4$ may be H or =O, but both are not =O. By selecting =O for $X_1$ or $X_2$, the N interposed between the carbons to which $X_1$ and $X_2$ are bonded will be an amide. Likewise, by selecting =O for $X_3$ or $X_4$, the N interposed between the carbons to which $X_3$ and $X_4$ are bonded will be an amide. Thus, a compound with zero, one or two amides may be formed by the appropriate selection of $X_1$, $X_2$, $X_3$ and $X_4$. Amide nitrogens, relative to amine nitrogens, afford greater stability to the complex formed with a metal, but at the expense of a diminished acceleration of complex formation. Thus, by selection of $X_1$, $X_2$, $X_3$ and $X_4$, compounds with a wide variety of chelating properties may be formed.

A is a hydrogen (H), alkyl group of $C_6$ or less, —CH$_2$—CH$_2$—S—R$_1$ or —CO—CH$_2$—S—R$_1$, except when either $X_1$ or $X_2$ is =O, A is H. Similarly, A' is H, alkyl group of $C_6$ or less, —CH$_2$—CH$_2$—S—R$_2$ or —CO—CH$_2$—S—R$_2$, except when either $X_3$ or $X_4$ is =O, A' is H. Y is —CH$_2$—S—R$_3$, or H, when A is H or an alkyl group of $C_6$ or less and A' is H or an alkyl group $C_6$ or less. Alternatively, when either A or A' or both are not H or an alkyl group of $C_6$ or less, then Y is H. Similarly, Y' is —CH₂—S—R₄, or H, when A is H or an alkyl group of C₆ or less and A' is H or an alkyl group of C₆ or less. However, Y and Y' are both not H when A is H or an alkyl group of C₆ or less and A' is H or an alkyl group of C₆ or less. Alternatively, when either A or A' or both are not H or an alkyl group of C₆ or less, then Y' is H. Thus, compounds of the formula depicted above may be formed containing two nitrogens and three or four sulfurs ("N₂S₃" and "N₂S₄", respectively). For "N₂S₄" compounds, two of the sulfurs are the sulfurs bearing R₅ and R₆ and the remaining two sulfurs are from A and A' or Y and Y'. The following formulae depict examples of N₂S₄ compounds in which two sulfurs are from Y and Y' (IA) or in which two sulfurs are from A and A' (IB).

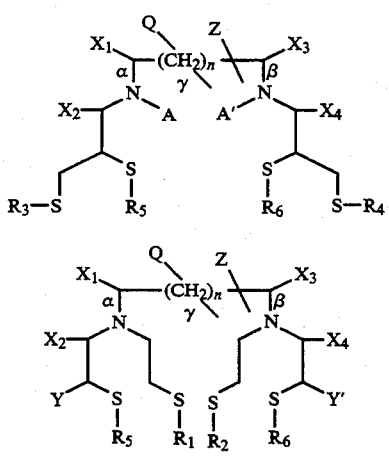

R₁, R₂, R₃, R₄, R₅ and R₆ are independently IB selected from sulfur protecting groups. Groups which may be used include any of the alkyl, acyl and aryl groups, disulfides and bunte salts known by those skilled in the art. Preferred groups are those that result in the formation of a thioacetal, hemithioacetal, thioester or acetamidomethyl substituent. Particularly preferred groups include p-anisylidine, acetonyl, tetrahydrylfuranyl, ethoxyethyl, tetrahydrylpyranyl, acetamidomethyl and derivatives thereof. When conjugated to a targeting agent, the protecting groups may be removed and left as sulfydryls either during storage or just prior to radiolabeling.

Q may be H or a polar group. One function of a polar group is to increase the hydrophilicity of the compound, e.g., in order to increase its aqueous solubility. Groups which may be used include carboxylates, sulfonates and secondary alcohols. A preferred group is —CH₂—COOH. Q may be attached to one of the positions designated as α, β, and γ. Because the number of methylene carbons at the γ position is defined by n which may be greater than one, the γ position includes additional points for attachment of Q.

The distance by which the nitrogen atoms are separated may be increased by interposing methylene (—CH₂—) groups between the carbons bonded to the nitrogens. When the number of —CH₂— groups, represented by n, is greater than zero, then the number of carbon atoms separating the nitrogen atoms in compound I is increased accordingly. Preferred integers for n are 0 to 2.

Z is —(W)ₘ—R'. W is a group that functions as a "spacer arm" and may be useful to distance R' from the chelating portion of the compound. Groups which may be used include methylene (—CH₂—), methyleneoxy (—CH₂—O—), methylenecarbonyl (—CH₂—CO—), or combinations thereof. The number, m, of groups such as these would be typically 0 to 30 and preferably 0 to 5.

Z, or R' when m is 0, may be attached to one of the positions designated as α, β, and γ. Because the number of methylene carbons at the γ position is defined by n which may be greater than one, the γ position includes additional points for attachment of a Z or an R'.

R' is a chemically reactive moiety. The moiety may be strongly electrophilic or nucleophilic and thereby be available for reacting directly with a targeting agent. Alternatively, the moiety may be a weaker electrophile or nucleophile and therefore require activation prior to the conjugation with a targeting agent. This alternative would be desirable where it is necessary to delay activation of R' until a compound has been formed. In either scenario R' is chemically reactive, the scenarios differ by whether following formation of a compound, R' is reacted directly with a targeting agent or is reacted first with one or more chemicals to render R' capable of reacting with a targeting agent. A discussion of reactions illustrative of a direct reaction with R' and of activation of R' is found below.

A metal chelate is formed by addition of a metal or metal oxide to compound I and has the following formula:

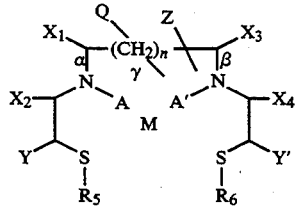

wherein: X₁-X₄, A, A', Y, Y', R₁-R₆, Q, n, and Z are defined as described above. M is a metal, or metal oxide, capable of being chelated. Preferred metals and metal oxides are those that are radionuclides. Particularly preferred are ⁶⁴Cu, ⁶⁷Cu, ⁹⁷Ru, ⁹⁹ᵐTc, ¹⁰⁵Rh, ¹⁰⁹Pd, ¹⁸⁶Re, ¹⁸⁸Re, ¹⁹⁸Au, ¹⁹⁹Au, ²⁰³Pb, ²¹²Pb, and ²¹²Bi.

The following formulae depict chelation of M by a compound I in which two of the sulfurs are from Y and Y' (I-M-A) and by a compound I in which two of the sulfurs are from A and A' (I-M-B). The six atoms available for bonding M are shown. Depending on the particular metal or metal oxide, M may be bound to 4–6 of the nitrogen and sulfur atoms of compound I.

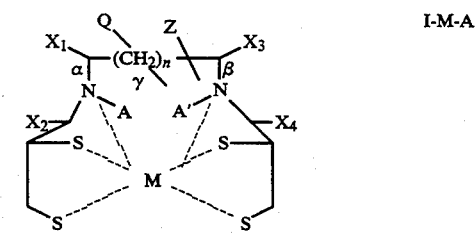

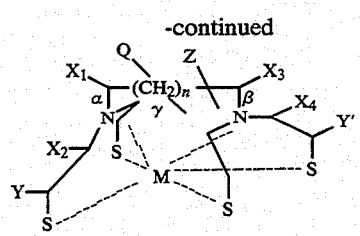

I-M-B

In addition to chelating compound I and the metal chelates therefrom, the invention provides chelate-targeting agent conjugates having the formula:

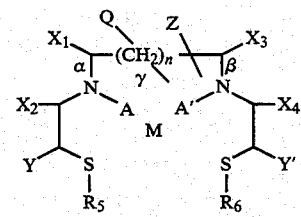

wherein: $X_1-X_4$, A, A', Y, Y', $R_1-R_6$, Q, n and M are defined as described above. Z' is $-(W)_m$-Targeting agent.

W is a group that functions as a "spacer arm" and may be useful to distance a targeting agent from the compound. Groups which may be used include methylene ($-CH_2-$), methyleneoxy ($-CH_2-O-$), methylenecarbonyl ($-CH_2-CO-$), or combinations thereof. The number, m, of groups such as these would be typically 0 to 30 and preferably 0 to 5.

Z', or Targeting agent when m is 0, may be attached to one of the positions designated as α, β, and γ. Because the number of methylene carbons at the γ position is defined by n which may be greater than one, the γ position includes additional points for attachment of a Z' or a Targeting agent.

The term targeting agent includes any linking group that may be used to join the targeting agent. It will be evident to one skilled in the art that a variety of linking groups, including bifunctional reagents, may be employed within the present invention.

As noted above, a targeting agent has the capacity to bind to a defined population of cells. The targeting agent may bind through a receptor, substrate, antigenic determinant, or other binding site on the target cell population. Preferred targeting agents useful within the present invention include antibody and antibody fragments; peptides, such as bombesin, gastrin-releasing peptide, RGD peptide, substance P, neuromedin-B, neuromedin-C, and metenkephalin; and hormones, such as estradiol, neurotensin, melanocyte stimulating hormone, follicle stimulating hormone, lutenizing hormone, and human growth hormone. Other suitable targeting agents include serum proteins, fibrinolytic enzymes, and biological response modifiers, such as interleukin, interferon, erythropoietin and colony-stimulating factor. Analogs of the above-listed targeting agents that retain the ability to bind to the defined target cell population may also be used within the claimed invention. In addition, synthetic targeting proteins and peptides may be designed and made to "fit" a particular, characterized epitope (binding site). That is, a synthetic targeting protein/peptide would be designed to bind a specific epitope in a "lock and key" fashion. Within the present invention, antibody and antibody fragments, bombesin and gastrin-releasing peptide and their analogs are particularly preferred targeting agents.

Preferred antibodies are monoclonal antibodies (MAbs). Particularly preferred are MAbs directed against tumor cells. Examples of such MAbs include those designated NR-ML-05, NR-LU-10, NR—CO—02, and NR-CE-01, which are specific for human melanoma, lung, colon, and lung tumor cells, respectively.

Two methods are provided for producing a chelate-targeting agent conjugate having the formula depicted immediately above. In the first method, a chelate is formed which is then joined to a targeting agent to form the conjugate. This method comprises the steps of reacting a compound (I) having the formula:

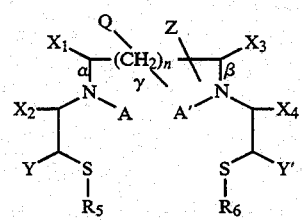

with a metal or, metal oxide capable of being chelated, thereby forming a metal chelate, and combining the metal chelate with a targeting agent under reactive conditions to form the chelate-targeting agent conjugate. $X_1-X_4$, A, A', Y, Y', $R_1-R_6$, Q, n, and Z are defined as described above. The preferred, and particularly preferred, metals and metal oxides are also described above. The discussion provided above regarding targeting agent is applicable here as well.

In the second method for producing a chelate-targeting agent conjugate, a chelating compound is joined to a targeting agent to form a conjugate to which a metal or metal oxide is added. This method comprises the steps of combining a compound (I) having the formula:

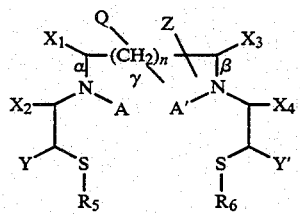

with a targeting agent under reactive conditions to form a derivatized targeting agent and reacting the derivatized targeting agent with a metal, or metal oxide, capable being chelated, thereby forming the chelate-targeting agent conjugate $X_1-X_4$, A, A', Y, Y', $R_1-R_6$, Q, n, and Z are defined as described above. The preferred, and particularly preferred, metals and metal oxides are also described above. The discussion provided above regarding targeting agent is applicable here as well.

Thus, the two methods for producing a chelate-targeting agent conjugate have a different order for the addition of the targeting agent. In the first method the targeting agent is joined to the chelate, i.e., after a metal or metal oxide has been added to a chelating compound. Conversely, in the second method the targeting agent is joined to the chelating compound, i.e., before a metal or metal oxide has been added. In both methods, however, a chelate-targeting agent conjugate has a targeting agent joined via R'. As noted above, a targeting agent may be joined by a direct reaction with R' or following the activation of R'.

The step of combining a targeting agent with a chelate or chelating compound may be performed by direct reaction of the targeting agent with R' on the chelate or chelating compound. Alternatively, it may be desirable to include a preparatory step before the step of combining. For example, a targeting agent may be modified in preparation for a direct reaction with R'. The modification of a targeting agent includes reaction with any of the numerous bifunctional reagents reported in the literature.

A direct reaction with R' by modified or unmodified targeting agent is intended to mean that R' is capable of reacting with the modified or unmodified targeting agent. For example, R' may be an alkyl group containing a good leaving group, e.g., a halide, or a carbonyl-containing group, such as an anhydride, acid halide, or "active ester." The term "active ester" is known to refer to esters which are highly reactive in nucleophilic substitution reactions. In the present invention, the modified or unmodified targeting agent would be the nucleophile. Typically the esters will be activated phenols and cyclic compounds based on hydroxylamine. Examples of commonly used ester groups are tetrafluorophenyl, N-hydroxysuccinimidyl, nitrophenyl, isothiocyanate and substituted isothiocyanates. Alternatively, R' may be a nucleophilic group, such as an amino or sulfhydryl group, which is capable of reacting with a modified targeting agent, e.g., containing a maleimide group.

Another way to perform a step in preparation for the step of combining a targeting agent and a chelate or chelating compound is to convert R' to a form capable of reacting with the targeting agent. Examples of conversions of R' include where R' is a carboxyl group and is then activated. Activation of a carboxyl group includes formation of an "active ester" as defined above. Another example of a conversion is where R' is a succinimide derivative containing a protective group, such as phenylsulfonyl. Upon removal of the group, the succinimide is converted to a maleimide which is highly reactive in nucleophilic addition reactions. Alternatively, R' may be a nucleophilic group, such as an amino or sulfhydryl group, and the conversion comprises reaction with a bifunctional reagent. It will be evident to one skilled in the art that a variety of bifunctional reagents, both homobifunctional and heterobifunctional, may be employed within the present invention.

As noted above, the present invention provides compounds of two formulae that are capable of chelating metals. Compound II, which contains three nitrogens and three sulfurs ("N₃S₃"), has the following formula:

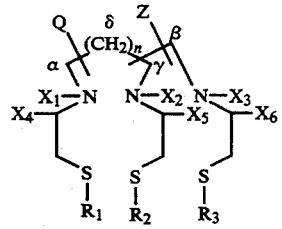

Examples of specific embodiments of the elements of compound II include the following.

$R_1$, $R_2$, and $R_3$ are independently selected from sulfur protecting groups. Groups which may be used include any of the alkyl, acyl, aryl groups, disulfides and bunte salts known by those skilled in the art. Preferred groups are those that result in an acyl, a thioacetal or a hemithioacetal. Particularly preferred groups include thioesters, p-anisylidine, acetonyl, tetrahydrylfuranyl, ethoxyethyl, tetrahydrylpyranyl, acetamidomethyl, and derivatives thereof.

$X_1$ and $X_2$ are independently selected from hydrogen (H) and an alkyl group of $C_6$ or less. $X_3$ is an H, an alkyl group of $C_6$ or less, or Z. $X_4$, $X_5$, and $X_6$ are independently selected from H and $=O$. The selection of $=O$ results in the presence of an amide. Thus, a compound with zero, one, two or three amides may be formed by the appropriate selection of $X_4$, $X_5$, and $X_6$. Amide nitrogens, relative to amine nitrogens, afford greater stability to the complex formed with a metal, but at the expense of a diminished acceleration of complex formation. Thus, by selection of $X_4$, $X_5$, and $X_6$, compounds with a wide variety of chelating properties may be formed.

Q may be H or a polar group. One function of a polar group is to increase the hydrophilicity of the compound, e.g., in order to increase its aqueous solubility. Groups which may be used include carboxylates, sulfonates and secondary alcohols. A preferred group is $-CH_2-COOH$. Q may be attached to one of the positions designated as $\alpha$, $\beta$, $\gamma$ and $\delta$. Because the number of methylene carbons at the $\delta$ position is defined by n which may be greater than one, the $\delta$ position includes additional points for attachment of Q.

The distance by which the nitrogen atoms are separated may be increased by interposing methylene ($-CH_2-$) groups between the carbons bonded to the nitrogens. When the number of $-CH_2-$ groups, represented by n, is greater than zero, then the number of carbon atoms separating the nitrogen atoms in compound II is increased accordingly. Preferred integer, s for n are 0 to 4.

Z is $-(W)_m-R'$. W is a group that functions as a "spacer arm" and may be useful to distance R' from the chelating portion of the compound. Groups which may be used include methylene ($-CH_2-$), methyleneoxy ($-CH_2-O-$), methylenecarbonyl ($-CH_2-CO-$), or combinations thereof. The number, m, of groups such as these would be typically 0 to 30 and preferably 0 to 5.

Z, or R' when m is 0, may be attached to $X_3$ or to one of the positions designated as $\alpha$, $\beta$, $\gamma$, and $\delta$. Because the number of methylene carbons at the $\delta$ position is defined by n which may be greater than one, the $\delta$ position includes additional points for attachment of a Z or an R'.

R' is a chemically reactive group and the discussion of it provided above for compound I is applicable here as well.

In compound II, the carbon designated as $\beta$ may be bonded to any one of the carbons designated as $\alpha$, $\gamma$ and $\delta$. The following formulae depict compounds in which the carbon is bonded to the $\gamma$ carbon (IIA) and the $\beta$ carbon is bonded to the $\delta$ carbon (IIB).

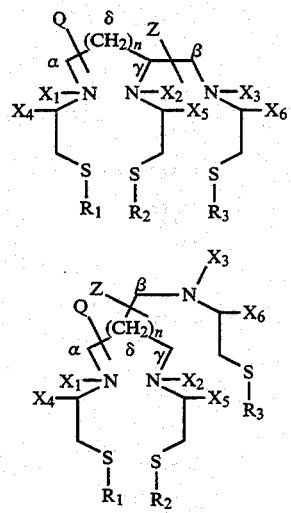

IIA

IIB

A metal chelate is formed by addition of a metal or metal oxide to compound II and has the following formula:

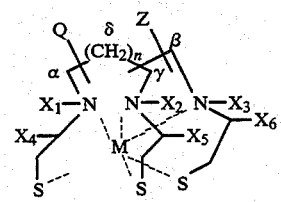

wherein: $R_1$–$R_3$, $X_1$–$X_2$, $X_3$, $X_4$–$X_6$, Q, n, and Z are defined as described above. M is a metal, or metal oxide, capable of being chelated. The six atoms available for bonding M are shown. Depending on the particular metal or metal oxide, M may be bound to 4–6 of the nitrogen and sulfur atoms of compound II. Preferred metals and metal oxides are those that are radionuclides. Particularly preferred are $^{64}$Cu, $^{67}$Cu, $^{97}$Ru, $^{99m}$Tc, $^{105}$Rh, $^{109}$Pd, $^{186}$Re, $^{188}$Re, $^{198}$Au, $^{199}$Au, $^{203}$Pb, $^{212}$Pb, and $^{212}$Bi.

In addition to chelating compound II and the metal chelates therefrom, the invention provides chelate-targeting agent conjugates having the formula:

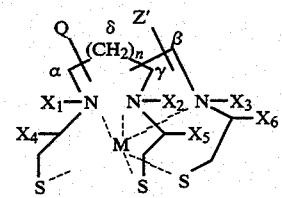

wherein: $R_1$–$R_3$, $X_1$–$X_2$, $X_3$, $X_4$–$X_6$, Q, n, and M are defined as described above. Z' is —(W)$_m$-Targeting agent.

W is a group that functions as a "spacer arm" and may be useful to distance a targeting agent from the compound. Groups which may be used include methylene (—CH$_2$—), methyleneoxy (—CH$_2$—O—), methylenecarbonyl (—CH$_2$—CO—), or combinations thereof. The number, m, of groups such as these would be typically 0 to 30 and preferably 0 to 5.

Z', or Targeting agent when m is 0, may be attached to $X_3$ or to one of the positions designated as α, β, γ and δ. Because the number of methylene carbons at the δ position is defined by n which may be greater than one, the δ position includes additional points for attachment of a Z' or a Targeting agent.

The term targeting agent includes any linking group that may be used to join the targeting agent will be evident to one skilled in the art that a variety of linking groups, including bifunctional reagents, may be employed within the present invention. The discussion of targeting agent provided above for compound I-type conjugates is applicable here as well.

Two methods are provided for producing a chelate-targeting agent conjugate having the formula depicted immediately above. In the first method, a chelate is formed which is then joined to a targeting agent to form the conjugate. This method comprises the steps of reacting a compound (II) having the formula:

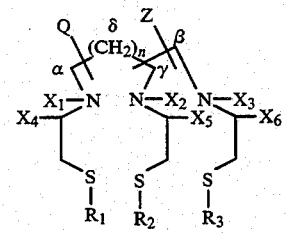

with a metal or metal oxide capable of being chelated, thereby forming a metal chelate, and combining the metal chelate with a targeting agent under reactive conditions to form the chelate-targeting agent conjugate. $R_1$–$R_3$, $X_1$–$X_2$, $X_3$, $X_4$–$X_6$, Q, n, and Z are defined as described above. The preferred, and particularly preferred, metals and metal oxides are also described above. The discussion provided above regarding targeting agent is applicable here as well.

In the second method for producing a chelate-targeting agent conjugate, a chelating compound is joined to a targeting agent to form a conjugate to which a metal or metal oxide is added. This method comprises the steps of combining a compound (II) having the formula:

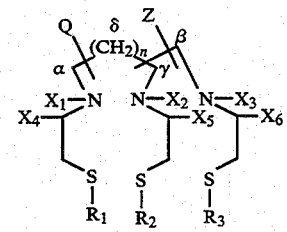

with a targeting agent under reactive conditions to form a derivatized targeting agent and reacting the derivatized targeting agent with a metal, or metal oxide, capable of being chelated, thereby forming the chelate-targeting agent conjugate. $R_1$–$R_3$, $X_1$–$X_2$, $X_3$, $X_4$–$X_6$, Q, n, and z are defined as described above. The preferred, and particularly preferred, metals and metal oxides are also described above. The discussion provided above regarding targeting agent is applicable here as well.

These two methods for producing a chelate-targeting agent conjugate using compound II are analogous to those provided above for the methods using compound I. The discussion above regarding the difference in the order of joining the targeting agent, the meaning of a direct reaction of a targeting agent with R', the modification of a targeting agent before the step of combining, and the conversion of R' before the step of combining, applies to the methods using compound II as well as those methods using compound I.

Another aspect of the invention provides kits for producing chelate-targeting agent conjugates for radiopharmaceutical use. Two types of diagnostic and therapeutic kits are prepared for use in the administration of chelate-targeting agent conjugates. The first type of kit ("pre-formed") comprises compound I, or compound II, and a targeting agent to be radiolabeled, each in separate containers. The compound is labeled with a metal, or metal oxide, radionuclide and then the resulting chelate is joined to the targeting agent. Thus, the radionuclide is added to the chelating compound prior to the addition of the targeting agent.

The second type of kit ("post-formed") comprises in one container compound I, or compound II, attached to a targeting agent to be radiolabeled and in another container a reducing agent and a complexing agent which in combination are capable of allowing a metal, or metal oxide, radionuclide to form an exchange complex. Thus, the radionuclide is added to the chelating compound after the addition of the targeting agent.

Preferred radionuclides for use in conjunction with a diagnostic kit are $^{99m}Tc$, $^{97}Ru$ and $^{203}Pb$ and with a therapeutic kit are $^{186}Re$, $^{188}Re$, $^{67}Cu$, $^{105}Rh$, $^{198}Au$, $^{199}Au$ and $^{212}Bi$. The discussion provided above regarding targeting agent is applicable here as well. The diagnostic and therapeutic kits, both in a pre-formed and a post-formed type, are described in detail in Example IV.

Yet another aspect of the invention provides methods for using the chelate-targeting agent conjugates described above for diagnostic and therapeutic purposes. The diagnostic method may be used to detect the presence or absence of a target site within a mammalian host. The method comprises the steps of administering to a mammal a diagnostically effective dose of one of the chelate-targeting agent conjugates described above, where the metal or metal oxide is a radionuclide and the conjugate is capable of binding to the target site. This step is followed by a step of detecting the biodistribution of the radionuclide in the mammal to determine the presence or absence of the target site in the host.

A diagnostically effective dose of a chelate-targeting agent conjugate is generally from about 5 to about 35 and typically from about 10 to about 30 mCi per 70 kg body weight. The precise dose for a chelate-targeting agent conjugate is dependent upon the particular targeting agent used because the level of uptake of a conjugate into a tumor is dependent upon the number of receptors for the targeting agent and its affinity for the receptors. The precise dose further depends upon the particular route of administration, e.g., intravenous, intracompartmental, intraarteoral or intratumoral. It will be evident to one skilled in the art how to determine the optimal effective dose for a particular chelate-targeting agent conjugate and a particular route of administration. The discussion provided above regarding targeting agent is applicable here as well. Preferred radionuclides are $^{97}Ru$, $^{99m}Tc$ and $^{203}Pb$. A preferred mammal is man.

The therapeutic method may be used for delivering a radionuclide to a target site within a mammalian host. The method comprises the step of administering to a mammal a therapeutically effective dose of one of the chelate-targeting agent conjugates described above, where the metal or metal oxide is a radionuclide and the conjugate is capable of binding to the target site. A therapeutically ;effective dose is generally from about 20 mCi to about 300 mCi. The discussion immediately above regarding the precise dose and the targeting agent portion of a chelate-targeting agent conjugate applies here as well. Preferred radionuclides are $^{186}Re$, $^{188}Re$, $^{67}Cu$, $^{105}Rh$ $^{198}Au$, $^{199}Au$ and $^{212}Bi$. A preferred mammal is man.

To summarize the examples which follow, Example I provides the preparation of chelating compounds. Example II describes the preparation of radiolabeled chelates and conjugation with targeting agents. Example III describes the preparation of targeting agent-chelating compound conjugates followed by radiolabeling of the conjugates. Example IV discloses kits for producing chelate-targeting agent conjugates. Example V describes biodistribution studies in mice. Example VI provides imaging of tumors in humans.

The following examples are offered by way of illustration and not by way of limitation.

EXAMPLES

EXAMPLE 1

Preparation of Chelating Compounds

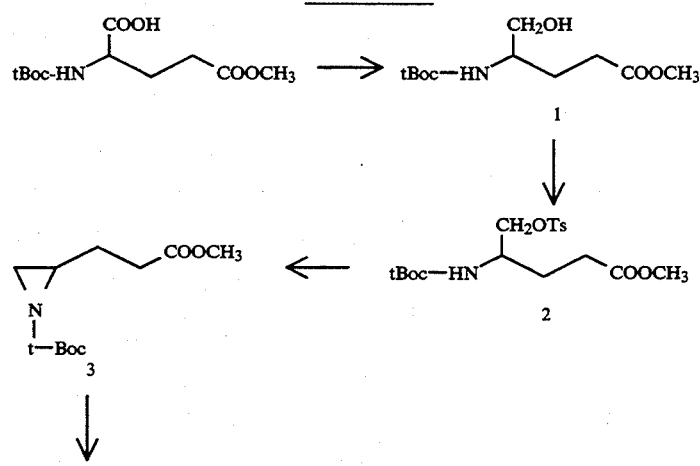

SCHEME 1

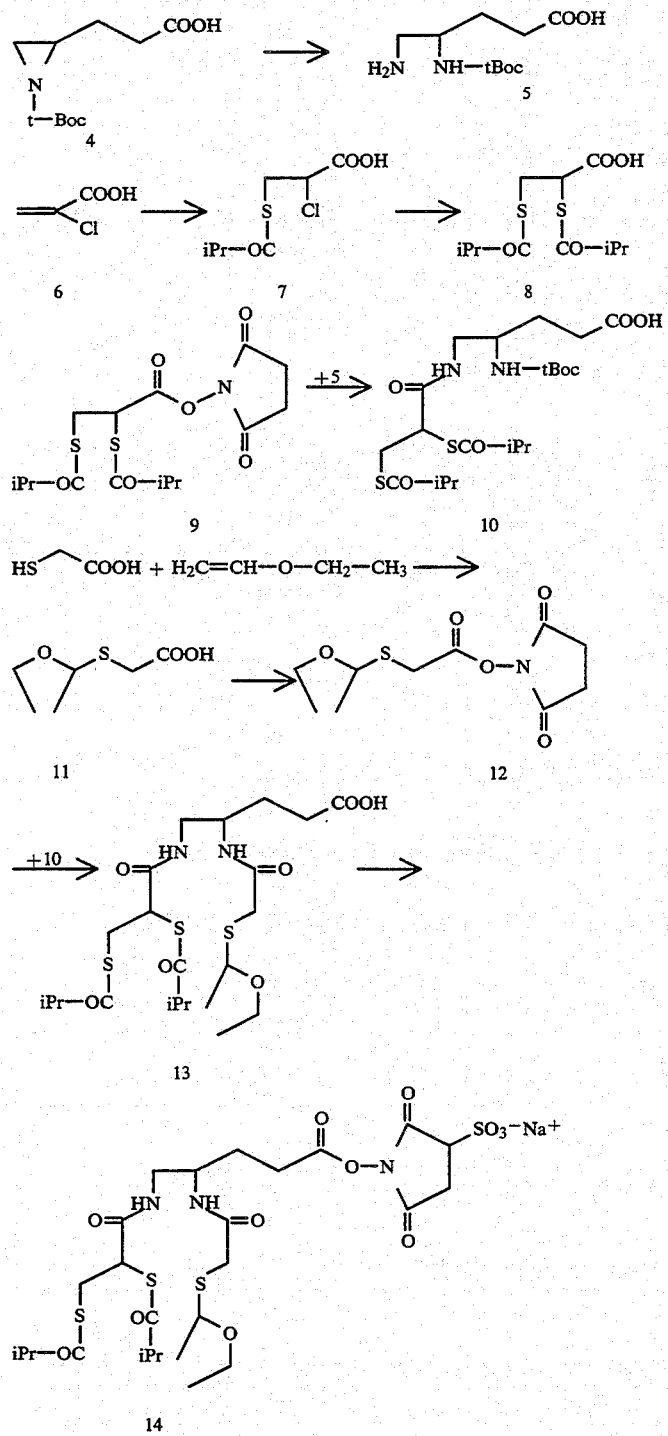

N-t-butoxycarbonyl-β-carbomethoxyethyl-aziridine 3

(i) N-t-butoxycarbonyl-L-glutamic acid-γ-methyl ester is prepared from L-glutamic acid-γ-methyl ester according to the procedure of R. K. Olsen and T. Emery., *J. Org. Chem.* 49:3527, 1984.

(ii) A 1.0M solution of borane.THF (0.68 mL, 0.68 mmol) is added to a solution of (143 mg, 0.55 mmol) in anhydrous tetrahydrofuran (0.68 mL). The reaction solution is stirred at ambient temperature for one hour and then quenched by the addition of 10 mL of methanol. The reaction solution is then evaporated to give an oil (160 mg). The oil is dissolved in 70 mL of ethyl acetate and washed with saturated NaHCO$_3$ (2×30 mL). The organic layer is dried over anhydrous MgSO$_4$ and evaporated in vacuo to give 1 as a colorless oil (120 mg, 88%).

(iii) p-Toluenesufonyl chloride (0.85 g, 4.46 mmol) is added to an ice cold (0°–5° C.) solution of 1 (1.00 g, 4.05 mmol) in pyridine (8 mL). The reaction solution is stirred at this temperature overnight. The reaction solution is diluted with methylene chloride (80 mL) and washed with pH 4.0 acetate buffer (3×70 mL), then with saturated bicarbonate (40 mL). The organic extract is repeatedly evaporated from toluene (to azeotrope the pyridine) to give the tosylate 2 as a brown viscous oil, which is used in the next step without further purification.

(iv) A solution of the tosylate 2 (1.38 g) in anhydrous dimethylformamide (3.0 mL) to a suspension of NaH (95 mg, 3.78 mmol) in DMF (1.5 mL). The reaction mixture is stirred for 1 hour, diluted with water (40 mL) and extracted with methylene chloride (3×40 mL). The combined methylene chloride extracts were dried (MgSO4) and evaporated to give a yellow oil (0.66 g). The oil is purified by flash chromatography over silica gel (1:1 ethyl acetate:hexanes) to give 3 as a pale yellow oil.

N-t-butoxycarbonylaziridine-3-propionic acid 4

To a solution of 1 mmol of 3 5 mL of ethanol is added 2 mL of 1N NaOH and the mixture is stirred for 2 hours at ambient temperature. The mixture is partitioned between 25 mL of water and 25 mL of ether. The aqueous layer is acidified to pH 2 and extracted with 2×25 mL of ether. The combined either extracts are washed with brine, dried with anhydrous MgSO4, filtered and concentrated to yield 4.

4-N-t-butoxycarbonylamino-5-amino-pentanoic acid 5

To a solution of 4 (1 mmol) in 5 mL of chloroform is added an excess of hydrazoic acid in chloroform. The mixture is stirred at ambient temperature and concentrated to give the azide. The azide is dissolved in 5 mL of isopropanol. To the solution is added 5 mmol of sodium borohydride. The mixture is refluxed for 16 hours, allowed to cool to ambient temperature and 5 mL of 1N HCl is added. The mixture is concentrated to give the crude hydrochloride salt of 5.

4-N-t-butoxycarbonylamino-5-(2′,3′-bis-S-isobutryl-dimercaptopropionamido)pentanoic acid 10

(i) 2-Chloro-3-mercaptoisobutryl propionic acid 7

To a solution of α-chloroacrylicacid 6 (1 mmol) in 10 mL of anhydrous methylene chloride containing 1.2 mmol of trifluoroacetic acid, 1.2 mmol of isothiobutyric acid is added. The solution is stirred for 2–3 hours at room temperature. The solvents are evaporated in vacuo, and the product is isolated by trituration with anhydrous ether. Trituration procedure is repeated several times to ensure complete removal of excess of the reagents that are used in the reaction.

(ii) 2,3-Bis(mercaptoisobutryl)propionic acid 8

A solution of 2-Chloro-3-mercapto-isobutryl propionic acid 7 (1 mmol) in 15–20 mL of i-propanol containing 1% water, 2 mmol of isothiobutyric acid is added and the solution is refluxed for 6–8 hours. The solvents are removed under reduced pressure and the product 3 is isolated by flash chromatography over silica gel. All the above mercapto compounds and derivatives have foul odor and will be handled in a well ventilated hood.

(iii) Succinimidyl 2,3-bis(mercaptoisobutryl) propionate 9

To a solution of 1 mmol of 2,3-bis (mercaptoisobutryl)propionic acid 8 in 10 mL of anhydrous tetrahydrofuran, 1.2 mmol of N-hydroxysuccinimide and 1.2 mmol of N,N′-dicyclohexylcarbodiimide is added and the solution is stirred at ambient temperature for overnight. The precipitated solid is filtered and the solvent is removed in vacuo. The residue is dissolved in ethyl acetate and the organic layer is washed with water. The ethyl acetate layer is dried, the solvent is removed and the product is purified by flash chromatography.

(iv) To a solution of 5 (1 mmol) in 1 mL of dimethylformamide is added 2 mmol of triethylamine followed by 1.1 mmol of the above succimimidate ester 9. The mixture is stirred for 2 hours at ambient temperature and dimethylformamide is removed in vacuo. The residue is partitioned between 1N HCl and ethyl acetate. The organic layer is dried with anhydrous MgSO4 and concentrated to give 10.

4-N-(S-1-ethoxyethylmercaptoacetamido)-5-(2′,3′-bis-S-isobutyryl-dimercaptopropionamido)-pentanoic acid 13

(i) S-(1-ethoxy)ethylmercaptoacetic acid 11

To a solution of 17.38 g of p-toluenesulfonic acid maintained between −18° C.–25° C., 23.9 mL of ethylvinyl ether in. 125 mL of dichloromethane is added in drops over a period of 1–1.5 hours. When the addition is complete, the mixture is stirred for another 1 hour. To the above cold solution 250 mL of pH 7 phosphate buffer is added and the cold mixture is poured into a mixture of 800 mL of ethyl acetate and 200 mL of water. The organic layer is removed and the aqueous layer is extracted with 2×200 mL of ethyl acetate. The combined layers were washed with brine, dried over anhydrous MgSO4 and evaporated to give S-(1-ethoxy)ethylmercaptoacetic acid 11 in 100 mL of dry tetrahydrofuran were added 4.85 g of N-hydroxysuccinimide and 8.7 g of N,N′-dicyclohexylcarbodiimide. The mixture is stirred for 2–3 hours. TLC in EtOAc:hexanes:acetic acid 49:50:1 (p-anisaldehyde stain) showed the completion of the reaction. Dicyclohexylurea is removed by filtration and the filtrate is evaporated. The oily residue is dissolved in 50 mL of ethyl acetate and washed with water. The solution is dried over anhydrous MgSo4 and evaporated and the product is purified by silica gel flash column chromatography.

(iii) To 1 mmol of 10 in 5 mL of methylene chloride is added 2 mL of trifluoroacetic acid and the mixture is stirred for 1 hour and concentrated in vacuo to a viscous oil. Trituration with either yielded the trifluoroacetate salt as a white solid which is dissolved in 1 mL dimethylformamide. To the solution is added 5 mmol of triethylamine followed by 1.1 mmol of succinimidyl S-1-ethoxyethylmercaptoacetate 12. The mixture is stirred for 2 hours at ambient temperature and the solvent is removed in vacuo. The residue is partitioned between 25 mL of 1N HCl and 25 mL of ethyl acetate. The organic layer is dried with anhydrous MgSO4 and concentrated to give 13, which is purified by silica gel chromatography.

Sulfosuccinimidyl-4-N-(S-1-ethoxyethylmercaptoacetamido)-5-(2′,3′-bis-S-isobutyryl-dimercaptopropionamido) pentanoate 14

A solution of the above acid 13 (1 mmol) in 1:1 CH3CN:H2O is stirred with N-hydroxysulfosuccinimide and 3 mmol of 1-(3-dimethylaminopropyl)-3-ethylcarbodiimide hydrochloride for overnight at ambient temperature. The solvents are removed in vacuo and the active ester 14 is isolated by HPLC.

SCHEME 2

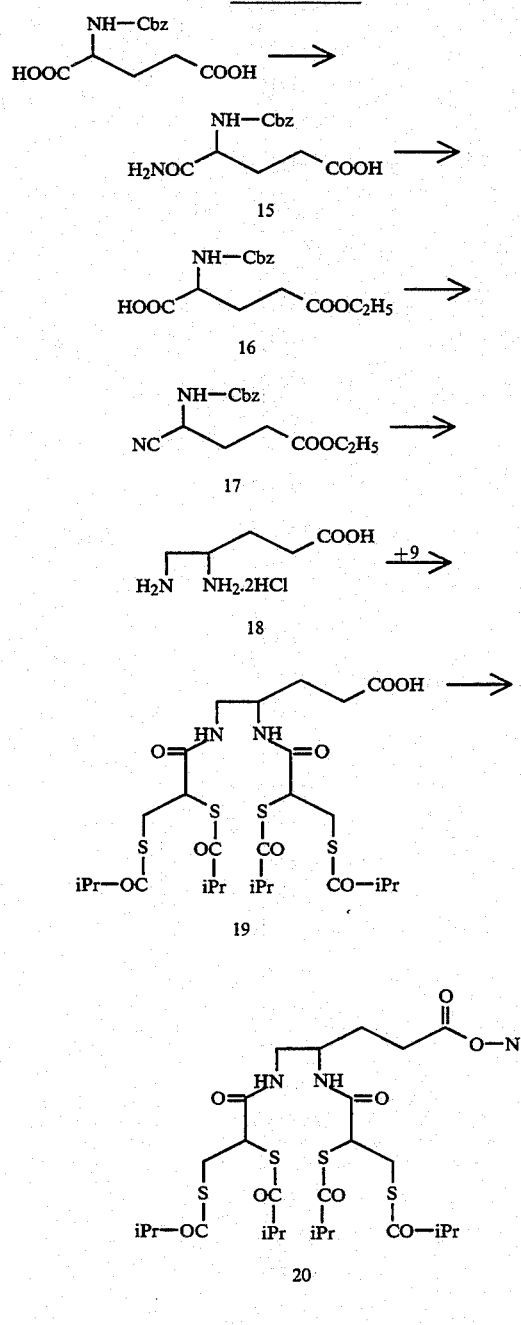

4,5-Diaminopentanoic acid 18

(i) N-Benyloxycarbonyl-L-isoglutamine 15 is prepared from N-Benyloxycarbonyl-L-glutamic acid according to the procedure of M. Itoh, *Chem. Pharm. Bull.* 17:8, 1986 (1969).

(ii) A suspension of 15.98 g of N-Benyloxy-carbonyl-L-isoglutamine in 500 mL of absolute ethanol containing 0.54 g of p-toluenesulfonic acid is refluxed for 12 hours until TLC indicated that the reaction is complete. The solution is concentrated to a small volume and addition f ether gave a solid. The solid is filtered and recrystallized to give 16.0 g of N-Benyloxycarbonyl-L-isoglutamine ethyl ester, 16.

(iii) To a suspension of 21.45 g of N-carbobenzoxy-carbonyl-L-isoglutamine ethyl ester in 200 mL of dry tetrahydrofuran kept at 0° C. to −5° C. in an ice-bath 11.82 mL of pyridine is added. To the above solution 9.84 mL of trifluoroacetic anhydride in 100 mL of tetrahydrofuran is added dropwise at such a rate that the bath temperature is maintained. The solution is stirred for 2 hours at this temperature. The solution is evaporated to dryness and the oil is dissolved in ethyl acetate. The organic layer is washed with 1.0N hydrochloric acid and sterile water. The solution is dried and evaporated in vacuo to give; an oil to give 14.8 g of ethyl γ-(N-carbobenzoxy)amino-γ-cyanobutanoate, 17.

(iv) A solution of 3.0 g of ethyl γ-(N-carbobenzoxy)amino-γ-cyanobutanoate in 80 mL of ethanol containing 80 mL of 6N HCl is hydrogenated at 60 psi over 0.5 g of $PtO_2$ in a Paar apparatus for 14-24 hours. The completion of reaction is checked by NMR and TLC. The catalyst is removed by filtration and the solvent is removed in vacuo. The thick syrup is dissolved in 100 mL of 6N HCl and stirred at 70° C. for approximately four hours. The solution is evaporated under vacuum to a thin oil. Addition of ethanol gave 4,5-diminopentanoic acid dihydro-chloride 18 as a solid. The solid is recrystallized from ethanol-water and dried in a vacuum dessicator.

Bis-4,5-(2′,3′-mercaptioisobuyryl)propionamido pentanoic acid 19

A solution of 4,5-diaminopentanoic acid 18 (1 mmol) in 10 mL of dimethylformamide is treated with 2.2 mmol of triethylamine and stirred for a few minutes. To this suspension 2.2 mmol of succinimidyl 2,3-bis (mercaptoisobutryl) propionate 9 (Scheme 1). The solution is stirred for 2 hours at ambient temperature. Dimethylformamide is removed in vacuo and the residue is dissolved in ethyl acetate and washed with water. The organic layer is dried with anhydrous sodium sulfate and evaporated to give 19.

Succinimidyl-bis-4,5-(2′,3′-mercaptoisobutyryl)propionamido pentanoate 20

To a solution of bis-4,5-(2′,3′-mercaptoisobutyryl) propionamido pentanoic acid 19 (1 mmol) in 10 ml of anhydrous tetrahydrofuran, N,N′-dicyclohexylohexyl-carbodiimide (1.2 mmol) and N-hydroxysuccinimide (1.2 mmol) is added. The mixture is stirred overnight at room temperature. Dicyclohexylurea is filtered and the solution is evaporated to dryness. The residue is dissolved in ethyl acetate and washed with water, dried with anhydrous $MgSO_4$ and evaporated to give 20. The product is purified by silica gel chromatography followed by HPLC.

SCHEME 3

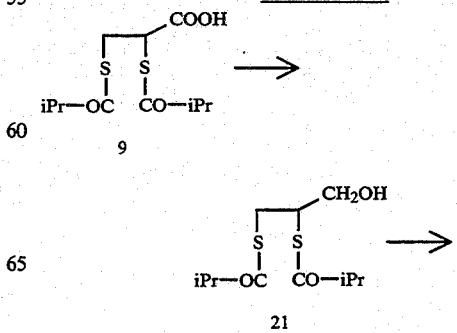

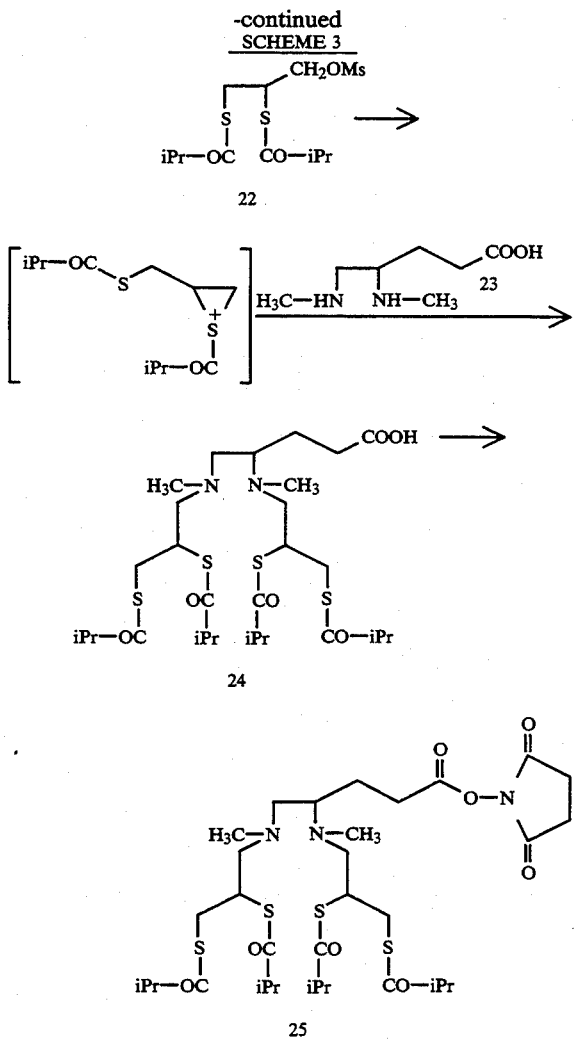

2,3-Bis(mercaptoisobutryl)propanol 21

To an ice-cold solution of 2,3-bis(mercaptoisobutryl) propionic acid 9 (Scheme 1) (1 mmol) in 10 mL of anhydrous tetrahydrofuran, 1.5 mL of 1M BH$_3$.THF is added over a period of 5 minutes (min.). The solution is stirred for another 10 min. and evaporated to dryness. Ten ml of water is added to the residue and the mixture is extracted with ethyl acetate. The organic layer is washed with water, dried and evaporated in vacuo to give the product 21, which is purified by flash column chromatography.

N,N'-Dimethyl-4,5-diaminopentanoic acid 23

To a solution of 4,5-diaminopentanoic acid (18; Scheme 2) (2 mmol) in 30 mL of anhydrous dimethylformamide, 5 mmol of di-t-butyldicarbonate is added and the solution is stirred overnight at room temperature. The solvent is removed in vacuo and the residue is crystallized to give N,N'-di-t-butoxycarbonylpentanoic acid.

To a solution of the above ester (1 mmol) in 10 mL of anhydrous dimethylformamide, 1 g of Ag$_2$O is added followed by 4 mmol of methyl iodide. The mixture is kept at 50° C. for 2 hours. The solid is filtered and evaporated. The residue is dissolved in methylene chloride and washed with water. Organic layer is evaporated and the product is purified by chromatography to give N,N'-dimethyl-N,N'-di-t-butoxycarbonyl-pentanoic acid methyl ester.

A solution of the above methyl ester is dissolved in 2 mL of ethanol and 10 mL 6N hydrochloric acid and refluxed for 5 hours. The aqueous solution is evaporated to dryness and the residue is dissolved in 5–10 mL of water. This process is repeated two more times and the residue is crystallized from ethanol-water to give N,N'-Dimethyl-4,5-diaminopentanoic acid 23 as dihydrochloride.

N,N'-Dimethyl-bis-4,5-(2',3'-mercaptoisobutyryl pentanoic acid 24

A solution of 21 (2 mmol) in 5 mL of methylene chloride containing 3 mmol of pyridine is cooled to 0° C. and 2.1 mmol of methanesulfonyl chloride is added. The solution is stirred at this temperature for 2 hours to give the mesylate 22 in-situ. The mesylate most likely is present as sulfonium ion. To this solution, a solution of 23 (1 mmol) in 5 mL of dimethyl formamide is added and stirred for 2 hours. The solution is allowed to come to room temperature and refluxed for another 2 hours. Evaporation of the solvent followed by chromatography yield the product, 24.

Succinimidyl-N,N'-dimethyl-bis-4,5-(2',3'-mercaptoisobutyryl)-propionyl pentanoate 25

The active ester is prepared by mixed anhydride method. A solution of the acid 24 (1 mmol) in 5 mL of anhydrous tetrahydrofuran and 2 mmol of 4-dimethylaminopyridine is cooled to −5° C. to 0° C. To this solution is added 1.1 mmol of isobutylchloroformate and stirred at this temperature for 10 min. A pre-cooled solution of N-hydroxysuccinimide (1.1 mmol) in 5 mL is added and the solution is stirred for another hour. Water is added and the mixture is evaporated. The residue is dissolved in 20 mL of methylene chloride and washed with water. The organic layer is dried and evaporated. The product 25 is isolated by reverse phase HPLC.

SCHEME 4

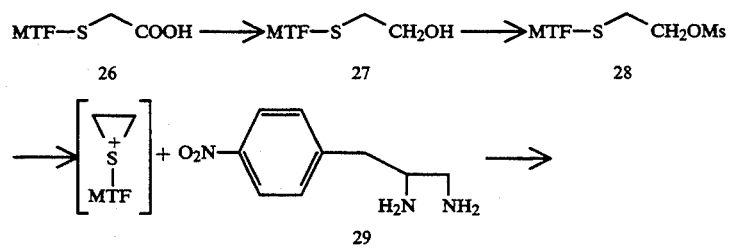

SCHEME 4

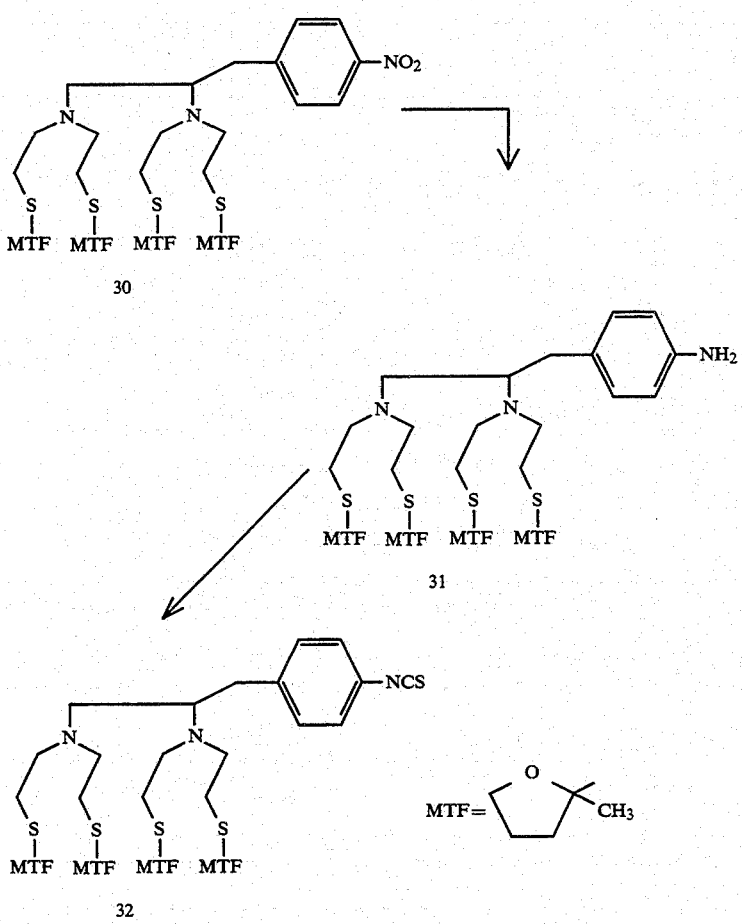

2-Carboxymethylthio-2-methyltetrahydrofuran 26

A solution of mercaptoacetic acid (10 mmol) in 5 mL of dichloromethane containing p-toluenesulfonic acid mono-hydrate (100 mg) is cooled with stirring to −10° to −25° C. 2-Methyl-4,5-dihydrofuran (10 mmol) in 10 mL of dichloromethane is added dropwise to the cold solution while the temperature is maintained between −10° C. to −25° C. Then 5 mL of phosphate buffer is added and the solution is allowed to come to room temperature. The mixture is poured into a 30 mL of ethyl acetate and 10 mL of water. Organic layer is separated and the aqueous layer is extracted with ethyl acetate. The combined ethyl acetate layer is dried and evaporated to give 26 as a colorless oil.

2-Hydroxyethylthio-2-methyltetrahydrofuran 27

To a solution of 2 mmol of 26 in 10 mL of anhydrous tetrahydrofuran (kept at 0° C.) 3 mL of $BH_3$. THF complex (1M) is added slowly. The mixture is stirred for 3 hours in a nitrogen atmosphere at 0° C. Approximately 10 mL of water added slowly and the reaction is stirred for 15 min. The mixture is concentrated in vacuo at 40°–45° C. and the aqueous residue is extracted with ethyl acetate. The organic layer is washed with 10% bicarbonate. The ethyl acetate layer is dried and evaporated to give the product, 27 as an oil.

2-Methylsulfonylmethylthio-2-methytetrahydrofuran 28

To a solution of 27 (2 mmol) in 10 mL of methylene chloride containing 2 mmol of triethylamine maintained at 0° C. is added methanesulfonylchloride (2 mmol) and the solution is stirred at room temperature for 1 hour. The mesylate 28 is unstable and hence the N-alkylation is carried out in situ without isolating the mesylate as described in the next step.

N,N,N′N′-Tetra-(S-2-methyltetrahydrofuran-2-yl)-β-mercaptoethyl-3-p-nitrophenyl-1,2-diaminopropane 30

To the above solution 0.5 mmol of 1,2-diamino-3-p-nitrophenylpropane 29 (prepared according to the procedure of L. H. DeRiemer, C. F. Meares, D. A. Goodwin and C. I. Diamanti, *J. of Labelled Compounds and Radiopharmaceuticals* 18:1517, 1981) is added and the solution is stirred at room temperature and refluxed for another 2–3 hours. The product is isolated by evaporation purified by silica gel chromatography.

N,N,N′,N′-Tetra-(S-2-methyltetrahydrofuran-2-yl)-β-mercaptoethyl-3-p-aminophenyl-1,2-diaminopropane 31

A solution of the nitro compound 30 (1 mmol) in 10 mL of absolute ethanol containing 100 mg of $PtO_2$ (Adams catalyst) is shaken in a Paar hydrogenator for 3 hours. The catalyst is removed by filtration and the solvent is removed in vacuo to yield the amino derivative 31, which is used in the next without further purification.

N,N,N'N'-Tetra-(S-2-methyltetrahydrofuran-2-yl)-β-mercaptoethyl-3-p-isothiocyanatophenyl-1,2-diaminopropane 32

To a solution of the above amino compound in 20 mL of methylene chloride is added. 1 mmol of thiocarbonyldiimidazole is added and the mixture is stirred at room temperature overnight. The solution is diluted with methylene chloride and washed with water. Evaporation and purification by liquid chromatography yields the isothiocyanate 32.

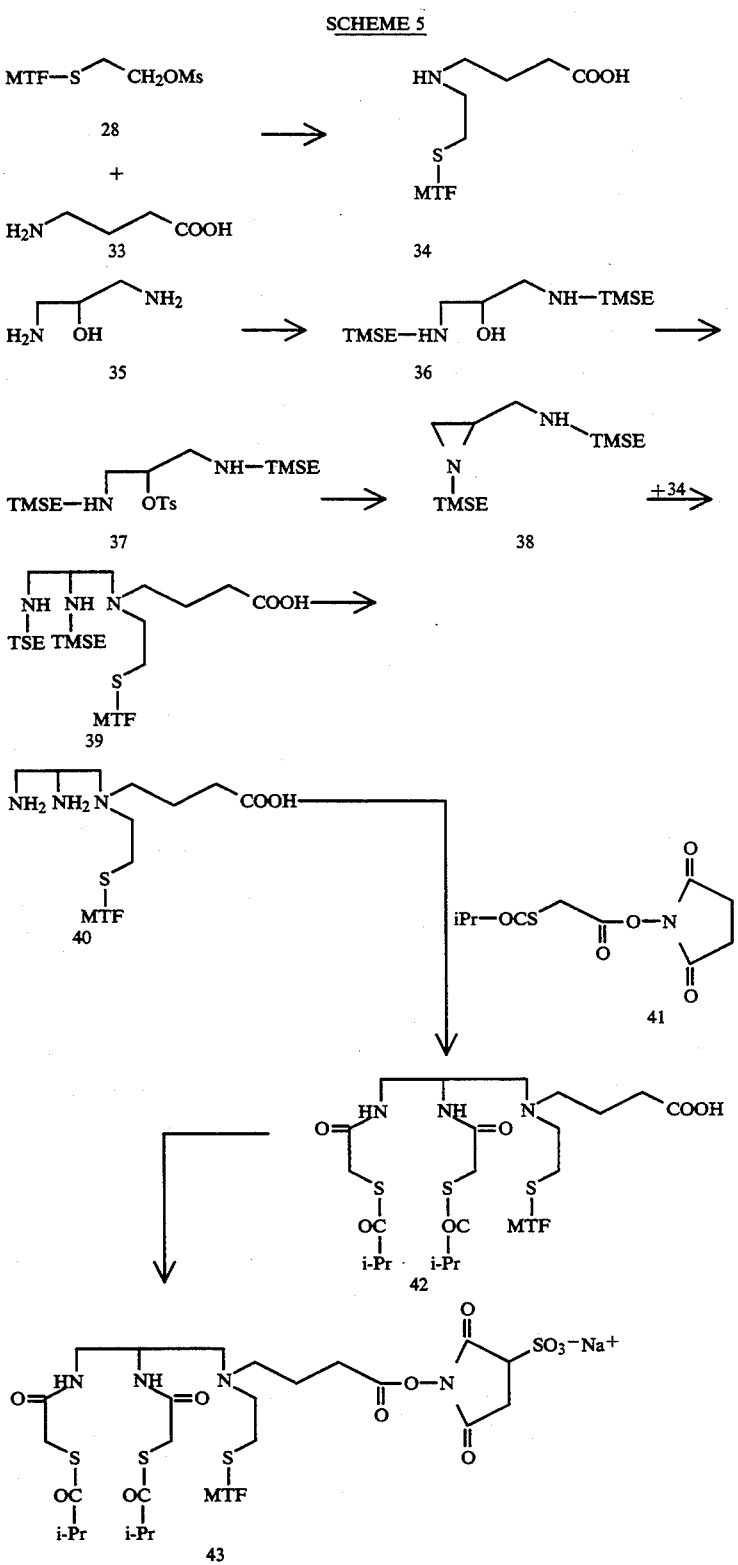

SCHEME 5

SCHEME 5

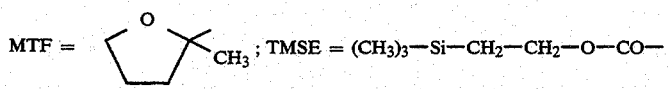 ; TMSE = (CH₃)₃—Si—CH₂—CH₂—O—CO—

N-(S-2'-Methyl-tetrahydrofuran-2-yl)-β-mercaptoethyl-γ-aminobutryic acid 34

A solution of 28 (1 mmol) (see Scheme 4) and γ-aminobutyric acid in 10 mL of methylene chloride and 2 mL pyridine is stirred for 10–15 hours at room temperature. The organic solvent is evaporated and the residue is dissolved in water. Acidification with glacial acetic acid precipitates the product, N-(S-2'-methyl-tetrahydrofuran-2-yl)-β-mercaptoethyl γ-aminobutyric acid 34.

1,3-(N,N'-Bis-β-trimethylsilylethoxycarbonyl)diamino-2-propanol 36

To a solution of 10 mmol of 1,3-diamino-2-propanol 35 in 30 mL of 5% sodium bicarbonate and 10 mL of methylene chloride 22 mmol of β-trimethylsilylethoxycarbonyl chloride is added and the mixture is stirred for 6 hours at room temperature. The organic layer is separated and the aqueous layer is extracted with 2×50 mL of methylene chloride. The combined organic layer is washed with water, dried and evaporated to give the product 26.

1,3-(N,N'-Bis-β-trimethylsilylethoxycarbonyl)diamino-2-O-(p-tosyl)propanol 37

To a solution of the above compound (2 mmol) in 5 mL of pyridine at 0° C., 2 mmol of p-toluenesulfonyl chloride is added and the mixture is stirred at this temperature for 2 hours and kept at 0° C. overnight. The mixture is poured into crushed ice to precipitate the product, which is purified by crystallization.

2-N-(β-Trimethylsilylethoxycarbonyl)-aminomethyl-1-(β)-Trimethylsilylethoxycarbonyl)-aziridine 38

To a solution of the above tosyl derivative (1 mmol) 27, in 5 mL of dry dimethylformamide, 1.1 mmol of sodium hydride is added and the solution is stirred for 2 hours at room temperature. The solvent is removed in vacuo and the residue is dissolved in ethyl acetate. The solution is washed with water, dried with anhydrous sodium sulfate and evaporated to give the aziridine derivative 28.

N-(S-2'-Methyl-tetrahydrofuran-2'-yl)-β-mercaptoethyl-N-(β,γ-di-trimethylsilylethoxycarbonylamino-propyl-γ-butyric acid 39

A solution of the aziridine derivative (1 mmol) 38, in 5 mL of acetonitrile is stirred under reflux with 1 mmol of N-(S-2'-Methyl-tetrahydrofuran-2-γ-1)-β-mercaptoethyl-γ-aminobutyric acid 34 at ambient temperature for 6 hours. Evaporation of the solvent in vacuo and purification of the residue by silica gel chromatography yields the desired product 39.

N-(S-2'-Methyl-tetrahydrofuran-2'-yl)-β-mercaptoethyl-N-(β,γ-diaminopropul)-γ-butyric acid 40

To a solution of 1 mmol of 39 in 5 mL of tetrahydrofuran, 2.5 mL of tetra-n-butylammonium floride is added and the solution is stirred for 30 minutes at room temperature. The solvent is removed in vacuo, the residue is dissolved in water and acidified to pH=3.5–4. The precipitated diamino acid 40 is filtered and dried.

S-Isobutrylmercaptoacetic acid succinimidate ester 41

(i) To a solution of 61 mg (0.47 mmol) of CoCl₂ in 20 mL of acetonitrile under nitrogen atmosphere is added dropwise over 15 minutes, a solution of 4.92 mL (5.0 g, 47 mmol) of isobutryl chloride and 2..97 mL (3.94 g, 43 mmol) of mercaptoacetic acid in 50 mL of acetonitrile. The mixture is stirred at room temperature for 2 hours and worked up by evaporating acetonitrile. The blue oil is partitioned between 50 mL of 0.1N HCl and 100 mL of either. The ether layer is washed with brine and concentrated to give an oil. Purification is done by silica gel column chromatography (26% ethyl acetate, 4% acetic acid, 70% hexanes) yielded 3.30 g (47%) of S-isobutrylmercaptoacetic acid as an oil: 1H NMR (CDCl₃): δ1.23 (d,6H), 2.84 (m,1H), 3.85 (s,2H).

(ii) To a solution of 3.30 g (20 mmol) of the above acid in 100 mL of methylene chloride at 0° C. is added 2.53 g (22 mmol) of N-hydroxysuccinimide followed by 4.52 g of N,N'-dicyclohexylcarbodiimide. The mixture is allowed to stir for 16 hours allowing the ice bath to equilibrate to room temperature. The mixture is chilled and filtered through celite. The filtrate is concentrated and purified by silica gel chromatography (50% EtOAc–50% hexanes) to give 4.48 g of 41 as a viscous oil: ¹H NMR (CDCl₃): δ1.23 (d,6H), 2.80 (m,1H), 2.81 (s,4H), 3.98 (s,2H).

N-(S-2'-Methyl-tetrahydrofuran-2'-yl)-β-mercaptoethyl-N-(β,γ-bis-S-isobutryl-mercaptoacetamido)-γ-butyric acid 42

To a solution of 1 mmol of 40 5 mL of dimethylformamide, S-isobutrylmercaptoacetic acid succinimidate ester 41 (2 mmol) is added and the solution is stirred for 3 hours at room temperature. The solvent is removed in vacuo and the residue is dissolved in ethyl acetate. The organic layer is washed with water, dried and evaporated to give 42.

N-(S-2'-Methyl-tetrahydrofuran-2'-yl)-β-mercaptoethyl-N-(β,γ-bis-S-isobutryl-mercaptoacetamido)-γ-butyric acid 43

To a solution of the above compound (1 mmol) in 5 mL of tetrahydrofuran containing 1 mmol of 4-dimethylaminopyridine kept at 0° C., 1 mmol of isobutylchloroformate is added and the solution is stirred for 20 mins. To this solution a pre-cooled solution of N-hydroxysulfosuccinimide (1 mmol) in 2 mL of anhydrous tetrahydrofuran is added. The solution is stirred for 1 hour and allowed to warm to room temperature. The solvent is removed in vacuo and the residue is dissolved in methylene chloride. The organic layer is washed with water, dried and evaporated to give the ester 43. Final purification is carried out by high pressure liquid chromatography.

SCHEME 6

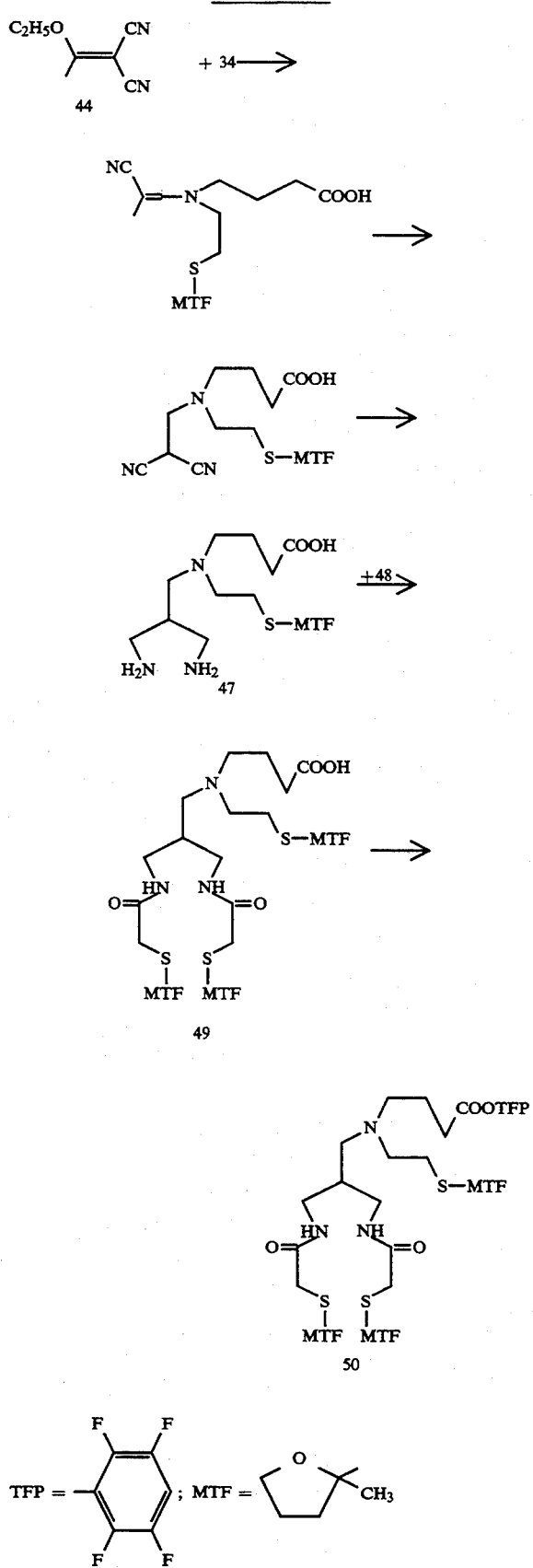

N-(β,β-Dicyano)ethylene-N-β-(S-2'-methyltetrahydrofuran-2-yl)mercapto-ethyl-γ-butyryic acid 45

An equimolar mixture of ethyoxyethylenemalononitrile 44 and compound 34 (scheme 5) are heated in an oil bath at 95° to 100° C. with an air condenser. The mixture is cooled to room temperature and the solidified mass is broken up in ethanol and filtered. The filtered solid is recrystallized.

N-β,β-Dicyano)ethyl-N-β-(S-2'-methyl-tetrahydrofuran-2-yl)mercapto-ethyl-butyryic acid 46

To a solution of the compound 45 (1 mmol) in 10 mL of isopropanol containing 1 gm of silica gel, 3 mmol of sodium borohydride is added and the mixture is stirred for 2-3 hours at room temperature. The silica gel is removed by filtration and the filtrate is evaporated to dryness. The residue is dissolved in ethyl acetate and washed with water, dried and evaporated to give the product. If necessary, the product is purified by silica gel flash chromatography.

N-β,β-Diaminomethyl)ethyl-N-β-(S-2'-methyltetrahydrofuran-2-yl)-mercapto-ethyl-γ-butyryic acid 47

A solution of the compound 46 (1 mmol) dissolved in 10 mL of ethanol containing 2 mmol of hydrogen chloride is hydrogenated at 50 psi in the presence of sulfided Pd-on carbon. After 10-12 hours the catalyst is removed by filtration and the filtrate is evaporated in vacuo. The product diamine 47 is used in the succeeding step without further purification.

N-(β,β-S-2'-methylmetetrahydrofuran-2-ylmercaptoacetamidomethyl)-ethyl-N-β-(S-2'-methylmetetrahydrofuran-2-yl)mercaptoethyl-γ-butyryic acid 49

(i) 2-methyl-tetrahydrofuran-2-yl succinimidate ester 48: This compound is prepared from 26 (scheme 4) and N-hydroxysuccinimide according to the general procedure described for the preparation of 12 (scheme 1).

(ii) To a solution of the above diamine 47 (1 mmol) in 5 mL of anhydrous dimethylformamide containing 2.1 mmol of triethylamine, 2.1 mmol of 2-methyl-tetrahydrofuran-2-yl succinimidate ester 48 is added and the mixture is stirred for 2-3 hours at room temperature. The solvent is removed in vacuo and the residue is dissolved in 10-15 mL of ethyl acetate. The organic layer is washed with water, dried over anhydrous sodium sulfate and evaporated. The product, 49 is purified by flash column silica gel chromatography.

N-(β,β-S-2'-methylmetetrahydrofuran-2-yl-mercaraptoacetamidomethyl)-ethyl-N-β-(S-2'-methylmetetrahydrofuran-2-yl)mercaptoethyl-γ-butyryic acid tetrafluorophenyl ester 50

A solution of the above acid (1 mmol) in 15-20 mL of tetrahydrofuran is stirred with 1.1 mmol of tetrafluorophenol and 1.1 mmol of N,N'-dicyclohexylcarbodiimide. After 8 hours at room temperature, the precipitated dicyclohexyl urea is filtered and the filtrate is evaporated to dryness. The residue in is dissolved in ethyl acetate and washed with water. The organic layer is dried over anhydrous sodium sulfate and evaporated to dryness. Trituration with ether to remove excess tetraflurophenol (in any present) gives the product 50. The final purification is carried out in HPLC.

SCHEME 7
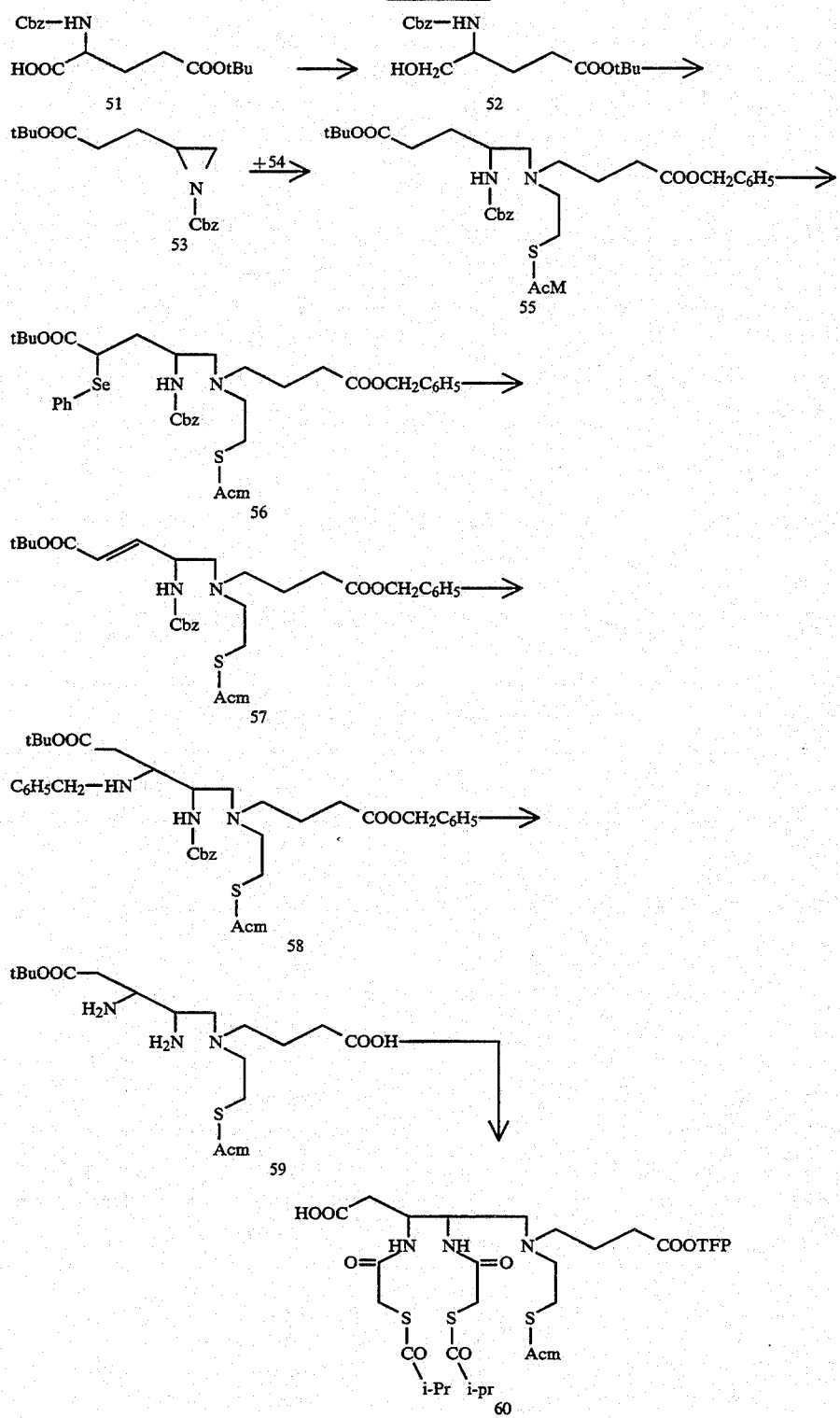
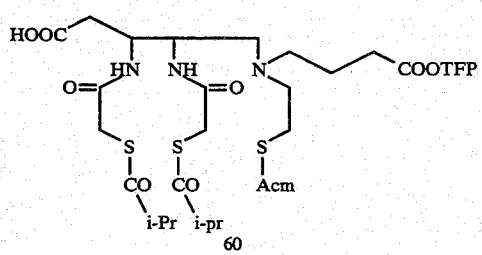
Acm = $CH_3-CO-NH-CH_2$
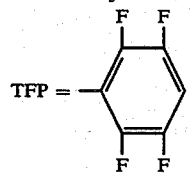

4-Hydroxymethyl-4-(t-butoxycarbonyl)aminobutanoic acid-t-butyl ester 52

Cbz-Glu-OtBu 51 is converted to 52 via the methyl ester followed by LiBH4 reduction according to the procedure of Y. Hamada, M. Shibata, T. Sugiura, S. Kato and T. Shioiri, *J. Org. Chem.* 52:1242, 1987 used for the conversion of t-Boc-Glu-OtBu to the corresponding alcohol.

N-t-Carbobenzyloxy-aziridine-propionic acid t-butyl ester 53

(i) p-Toluene sulfonyl chloride (1.1 mmol) is added to an ice-cold solution of 52 (1 mmol) in pyridine (5 mL). The reaction is stirred at this temperature overnight. The solution is diluted with 20 mL of methylene chloride and washed with pH 4.0 buffer and then with saturated bicarbonate. The organic extract is repeatedly evaporated with toluene giving the tosylate of 52 which is used in the next step without further purification.

(ii) A solution of the tosylate (1 mmol) in dimethyl-formamide (1 mL) is added to a suspension of NaH (1.1 mmol) in dimethylformamide (1 mL). The reaction mixture is stirred for one hour, diluted with water and extracted with methylene chloride. The organic layer is washed with water, dried over anhydrous MgSO4 and evaporated to glove 53. Purification is achieved by silica gel flash column chromatography.

5-N-(β-S-acetamidomethyl)ethyl-5-N-(γ-phenylacetyl)-propyl-4-N'-carbobenzyloxy)-4,5-diaminopentanoic acid-t-butyl ester 55

(i) S-Acetamido-methylmercaptoacetic acid is prepared according to the procedure of J. D. Milkowski, D. Veber, R. Hitchmann, *Org. Syn.* 59:190 using reaction condition similar to the one described for the preparation of S-acetamidomethyl-L-cysteine.

(ii) Reduction of the acid in step (i) to the alcohol, mesylation of the alcohol and displacement of the mesylate with γ-aminobutyric acid benzyl ester are accomplished to give N-(β-S-acetamidomethyl)ethyl-γ-aminobutyric acid benzyl ester 54 in a procedure similar to the one described in Scheme 4, for the preparation of 34.

(iii) To a solution of N-carbobenzyloxy-aziridine propionic acid t-butyl ester 53 (1 mmol) in anhydrous tetrahydrofuran (5 mL), is added 1 mmol of N-(β-S-acetamidomethyl)ethyl-γ-aminobutyric acid benzyl ester 54 (from step ii)) and the mixture is refluxed for 6-8 hours. The solvent is removed and the product 55 is purified by silica gel chromatography.

5-N-(β-S-acetamidomethyl)ethyl-5-N-(γ-phenylacetyl)-propyl-4-N'-(carbo-benzyloxy)-2-selenophenyl-4,5-diaminopentanoic acid-t-buty ester 56

Seleno-phenylation of 55 is carried out to yield 56 according to the procedure of R. B. Silverman, B. J. Invergo and J. Mathew, *J. Med. Chem.* 29(10):1840, 1986, similar to the one used for the preparation of methyl 4-[(benzyloxy-carbonyl)amino]-5-fluoropentenoate.

5-N-(β-S-acetamidomethyl)ethyl-5-N-(γ-phenylacetyl)-propyl-4-N'-(carbo-benzyloxy)-4,5-diamino-2-pentanoic acid-t-buty ester 57

Oxidation and elimination of selenoxy phenyl group in 56 to yield 57 is carried out according to the procedure of R. B. Silverman, B. J. Invergo and J. Mathew, *J. Med. Chem.* 29(10):1840, 1986, similar to the one used for the preparation of methyl 4-[(benzyloxy-carbonyl)amino]-5-fluoro-2-pentenoate.

5-N-(β-S-acetamidomethyl)ethyl-5-N-(γ-phenylacetyl)-propyl-3-N-benzyl-4-N'-(carbo-benzyloxy)-3,4,5-triamino-pentanoic acid-t-butyl ester 58

The preceding pentenoate 57 (1 mmol) is diluted with methanol (distilled from Mg) and 3 mmol of benzylamine is added. The reaction is stirred in nitrogen atmosphere at 45° to 50° C. for overnight. Evaporation of the solvent is carried out in vacuo and the product is isolated by silica gel chromatography.

5-N-(β-S-acetamidomethyl)ethyl-5-N-(γ-carboxy)propyl-3,4,5-tri-amino pentanoic acid-t-bury ester 59

A solution of 58 (1 mmol) in 20 mL of ethanol containing 3 equivalents hydrogen chloride is hydrogenated in a Paar apparatus over Pd-C (10%) for 24 hours. The catalyst is removed by filtration through celite and the solvent is removed in vacuo to yield the product.

5-N-(β-S-acetamidomethyl)ethyl-5-N-(γ-2,3,5,6-tetrafluorophenoxyacetyl)-propyl-3,4-bis-(S-isobutyrylmercaptoactamido)-3,4,5-triamino-pentanoic acid 60

(i) To a solution of the above compound (1 mmol) in 2-3 mL of dimethyl-formamide containing 3 mmol of triethylamine is stirred with S-isobutrylmercaptoacetic acid succinimidate ester (41: Scheme 5) for 6-8 hours. The solvent is removed by evaporation and the residue is dissolved in ethyl acetate. The organic layer is washed with water, dried and evaporated to give the product, 5-N-(β-S-acetamidomethyl)ethyl-5-N-(γ-phenoxyacetyl)-propyl-3,4-bis-(S-isobutyryl-mercaptoactamido)-3,4,5-triamino pentanoic acid-t-butyl ester.

(ii) The tetrafluorophenyl ester is of the preceding acid is prepared by mixed anhydride method according to the procedure described earlier for the preparation of 46 (see scheme 6).

(iii) The above mixed ester is dissolved in 20 mL of methylene chloride, to which ethereal hydrogen chloride is added. After few hours the precipitated solid is removed by filtration and washed with either to yield the final product, 60 as the hydrochloride salt. Final purification is carried out by liquid chromatography.

EXAMPLE II

Preparation of Radiolabeled Chelate and Conjugation with Antibody

A. Radiolabeling of Chelating Compounds

1. Technetium-99m labeling

Method a: To 100 μl of solution containing 5 mg of sodium gluconate and 0.1 mg of SnCl2 in water, at pH =6.1, 75–100 mCi of 1 mL. $^{99m}TcO_4$ (pertechnetate) is added. After incubation at room temperature for 10 min. to form a $^{99m}Tc$-gluconate complex, 100 μg of a chelating compound (see Example I) dissolved in i-propanol:acetic acid, 90:10, at 1 mg/mL, 80 μl of 0.2N HCl and 200 μL of i-propanol are added in that order. The reaction mixture is heated to 75° C. for 15 min., then cooled in ice for 5 min.

Method b: Alternatively, 1.0 mL of $^{99}Mo/^{99m}Tc$ generator eluted pertechnetate (75–100 mCi) is added to a vial containing a lyophilized mixture comprising sodium gluconate, stannous chloride, 0.1 mg; gentisic acid, 0.1 mg; lactose, 25 mg at pH 6.1. The vial is agitated gently to mix the contents by inversion and then incubated at room temperature for 10 mins.

2. Rhenium-188 labeling

The $^{188}$Re chelate of the chelating compound is prepared by a similar procedure. Sodium perrhenate (3 mL, 30 mCi/mL produced from a $^{188}$W/$^{188}$Re generator) is added to a vial containing a lyophilized mixture comprising citric acid, 75 mg; stannous chloride, 0.75 mg; gentisic acid, 0.25 mg and lactose, 100 mg. The vial is agitated gently to mix the contents, then incubated at room temperature for 10 min. To a separate vial containing 0.50 mg of the chelating compound, 0.50 mL of 2-propanol is added and the vial is agitated for 2 min. to completely dissolve the compound. Then 0.3 mL of this solution is transferred to the vial containing the $^{188}$Re-citrate complex. The reaction mixture is heated to 75° C. for 15 min., then cooled in ice for 5 min.

3. Rhenium-186 labeling

The $^{186}$Re chelate of the chelating compound is prepared by a procedure similar to the $^{188}$Re procedure. Perrhenate $^{186}$ReO$_4$ as sodium, lithium, ammonium or any other suitable counter ion is obtained from irradiation of $^{185}$Re (0.1 to few mg) in a nuclear reactor dissolution and purification of the original solution by previously described procedure (Venderhyden et al., *Inorg. Chem.* 24:1666, 1985) or any other suitable procedure. To the $^{186}$ReO$_4$ vial is added 0.75 mL reconstituted solution made of 1.0 mL of sterile water added to a vial containing a lyophilized mixture comprising citric acid 25 mg, stannous chloride 1 mg, gentisic acid 1 mg and lactose 75 mg.

The vial is agitated gently to mix the contents, then incubated at room temperature of 75° C. To the separate vial containing the chelating compound, 2-propanol is added to obtain a completely dissolved solution. An appropriate amount of this solution to give a ligand to rhenium mole ratio of 1:5 (preferentially between 1 and 1.5 ligand to rhenium mole ratio) is then transferred to the vial containing the $^{186}$Re-citrate complex. The reaction mixture is heated to 75° C. for 20 min. then cooled on ice for 5 min.

B. Conjugation of Radiolabeled Chelate with Antibody

To the above $^{99m}$Tc chelate, 100 μl of bicarbonate buffer is added so that the pH of the solution is about 6.0. Next, 400 μl of a solution containing antibody (or fragment) at 5 mg/mL is added in the same buffer. The antibody is a monoclonal antibody (or fragments thereof) designated as NR-ML-05, NR-LU-10, NR-CO-02, NR-CE-01 specific for human melanoma, lung, colon and CEA secreting tumor cells, respectively. The reaction mixtures are incubated at room temperature for 15-30 min. as necessary. The ITLC procedure (*Nuclear Medicine Technology and Techniques*, ed. Bernlet, D., Longan, J., and Wells, L.: The C. V. Mosby Co., St Louis, Mo., 1981; pp. 172-174) using 12% trichloroacetic acid is utilized to determine the percentage of chelate attached to the protein.

In the case of radiorheniums, an extra purification step is added depending on the form, e.g., F(ab')$_2$, of the antibody to be labeled. This step is designed to guarantee efficient labeling of the F(ab')$_2$ fragment, which is usually more susceptible to reduction into two Fab' fragments. However, the labeling approach is similar to technetium using the appropriate pH and volume of buffer for conjugation.

In all cases, the final purification of the antibody-chelate complex is achieved by passing the conjugate through an ion exchange (DEAE or QAE Sephadex) or gel permeation column (as sephadex G-25 or acrylamide gel). The purity of the conjugate is over 90% before administration to test animals and to humans. Aseptic techniques are used throughout the radiolabeled monoclonal antibody preparation for human administration.

EXAMPLE III

Preparation of Antibody-Chelating Compound Conjugate Followed by Labeling with $^{99m}$Tc or $^{188}$Re

A. Preparation of the Conjugate

The antibody conjugation reaction is performed in a final volume of 4.0 mL: 1 mg of the chelating compound (61.67 μmol), 1.1 mg of a monoclonal antibody (IgG, 7.8 mmol), 1-2 mL of distilled dimethyl formamide (if necessary to solubilize the chelating compound), 0.05M of borate or 0.5M bicarbonate buffer at pH 8.5. After stirring for 90 min. at room temperature, 4.4 mL of 5N sodium chloride is added. After an additional 30 min., the reaction mixture is centrifuged to remove any particulates and the supernatent is fractioned by gel filtration column chromatography. The column eluent is monitored at 280 nm and the fractions containing monomeric antibody conjugate are pooled and concentrated in an Amicon stirred cell (30,000 molecular weight cutoff).

B. Radiolabeling of the Conjugate

1. Technetium-99m labeling

Stannous tartrate kits were prepared from degassed solutions of 0.5 mL disodium tartrate (10 mg/mL) and 0.1 mL stannous chloride (1.0 mg/mL in ethanol) in an evacuated vial under nitrogen atmosphere. To a stannous tartrate kit at pH 6.0, sodium pertechnetate 0.5 mL (about 15 mCi) is added and allowed to stand at room temperature for 5 min. Quality control for $^{99m}$Tc-tartrate and insoluble $^{99m}$Tc is carried out on Gelman ITLC using methyl ethyl ketone and 0.01M sodium tartrate pH 7.0 eluents, respectively. $^{99m}$Tc-tartrate formation is typically 98-99% with insoluble $^{99m}$Tc values as TcO$_2$ ranging from 0.1 to 0.2%.

In an evacuated vial, 200 ul of sodium phosphate (0.2M, pH 8.0) and 200 ul of antibody-chelating compound conjugate (1.9 mg/mL) are added successively. Immediately after adding the conjugate, 250 ul of $^{99m}$Tc-tartrate (about 3 to 5 mCi is added and heated at 37° C. for 1 hour. The percent technetium bound to protein and the formation of pertechnetate are determined by ITLC using either 12% TCA or 50% MeOH: 10% ammonium acetate (1:1) and 1-butanol eluents, respectively. Technetium incorporation typically range from 70-90% on a chelating compound-Ab conjugate with a chelating compound per antibody ratio of 1.5 to 3.0.

2. Rhenium-188 labeling

The $^{188}$Re chelate form of the conjugate is prepared in a procedure similar to that described for $^{188}$Re above. Sodium perrhenate (3 mL, 15 mCi, produced from a $^{188}$W/$^{188}$Re generator) is added to a vial containing a lyophilized mixture comprising: citric acid, 75 mg; stannous chloride, 0.75 mg; gentisic acid, 0.25 mg; and lactose, 75 mg. The vial is agitated gently to mix the contents, then incubated at 75° C. for 15 min. to form a activated $^{188}$Re-citrate complex.

Labeling of the conjugate is carried out in a similar procedure described for $^{99m}$Tc above.

3. Rhenium-186 labeling

The $^{186}$Re chelate form of the conugate is obtained by a procedure similar to the $^{186}$Re labeling of the chelating compound described above. To the purified perrhenate vial is added 0.75 mL of the reconstituted solution made of 1.0 mL of sterile water added to a vial containing a lyophilized mixture comprising citric acid 15 mg, stannous chloride 1 mg, gentisic acid 1 mg and lactose 75 mg. The vial is incubated at 75° C for 15 min. then cooled for 5 min. to field $^{186}$Re-citrate complex ready for labeling of the conjugate. Labeling of the conjugate is carried out in a similar procedure described for Tc-99m with a protein to rhenium mole ratio varying from 0.2 to 10 (preferentially around 1).

EXAMPLE IV

Kits

Two different types, pre-formed and post-formed, of diagnostic and therapeutic kits are prepared for use in the administration of chelate-protein conjugates: (1) Conjugates from a chelate which is produced by radiolabeling a chelating compound followed by attachment to a protein, e.g., Example II, and (2) Conjugates produced by radiolabeling a chelating compound-protein conjugate, e.g., Example III.

A. Diagnostic Kit

1. Pre-formed: Technetium-99m labeling of chelating compound followed by conjugation of the chelate with an antibody.

A diagnostic kit containing reagents for preparation of a $^{99m}$Tc-radiolabeled protein conjugate is used as follows. The procedures are conducted under conditions which ensure the sterility of the product (e.g., sterile vials and sterilized reagents are used where possible, and reagents are transferred using sterile syringes). Proper shielding is used once the radioisotope is introduced.

One mL of sterile water for injection is added to a sterile vial containing a stannous gluconate complex (50 mg sodium gluconate and 1.2 mg stannous chloride dihydrate in dry solid form) and the vial is gently agitated until the contents were dissolved. A sterile insulin syringe is used to inject 0.1 mL of the resulting stannous gluconate solution into an empty sterile vial. Sodium pertechnetate (1.0 mL, 75–100 mCi, from a $^{99}$Mo/$^{99}$Tc generator available from DuPont, Mediphysics, Mallinckrodt or E.R. Squibb) is added, and the vial is agitated gently to mix the contents, then incubated at room temperature for 10 minutes to form a $^{99m}$Tc-gluconate complex.

In an alternative procedure for providing the $^{99m}$Tc-gluconate exchange complex, the kit includes a vial containing a lyophilized preparation comprising 5 mg sodium gluconate, 0.12 mg stannous chloride dihydrate, about 0.1 mg gentisic acid as a stabilizer compound, and about 20 mg lactose as a filler compound. The amount of gentisic acid may vary, with the stabilizing effect generally increasing up to about 0.1 mg. Interference with the desired reactions may occur when about 0.2 mg or more gentisic acid is added. The amount of lactose also may vary, with amounts between 20 and 100 mg, for example, being effective in aiding lyophilization. Addition of stabilizer and a filler compound is especially important when the vial contained these relatively small amounts of sodium gluconate and stannous chloride (compared to the alternative embodiment above). One mL of sodium pertechnetate (about 100 mCi) is added directly to the lyophilized preparation. The vial is agitated gently to mix the contents, then incubated as described above to form the $^{99m}$Tc-gluconate complex.

A separate vial containing 0.3 mg of a chelating agent in dry solid form is prepared by dispensing a solution of 0.3 mg chelating agent in 2-propanol into the vial, then removing the solvent under $N_2$ gas, and the resulting vial containing the chelating compound is provided in the kit. To this vial is then added 0.87 mL of 100% isopropyl alcohol, and the vial is gently shaken for about 2 minutes to completely dissolve the chelating agent. Next, 0.58 mL of this solution of the chelating agent is transferred to a vial containing 0.16 mL of glacial acetic acid/0.2N HCl (2:14), and the vial is gently agitated. Of this acidified solution, 0.5 mL is transferred to the vial containing the $^{99m}$Tc-gluconate complex, described above. After mixing gently by inversion, the vial is incubated in a 75° C.±2° C. water bath for 15 minutes, then immediately transferred to a 0° C. ice bath for 2 minutes.

To a separate vial containing 10 mg of the F(ab) fragment of a monoclonal antibody in 0.5 mL of phosphate-buffered saline, is added 0.37 mL of 1.0M sodium bicarbonate buffer, pH 10.0. The F(ab) fragment is generated by treating the monoclonal antibody several times with papain according to conventional techniques and dialyzed PBS to eliminate TRIS buffer. The vial is gently agitated.

The vial containing the acidified solution of the $^{99m}$Tc-labeled chelate (see above) is removed from the ice bath, 0.1 mL of the sodium bicarbonate buffer is added, and the vial is agitated to mix. Immediately, the buffered antibody solution (above) is added, gently agitated to mix and incubated at room temperature for 20 minutes to allow conjugation of the radiolabeled chelate to the antibody.

A column containing an anion exchanger, either DEAE-Sephadex or QAE-Sephadex, is used to purify the conjugate- A 5 mL QAE Sephadex column is washed with 5 mL of 37 mM sodium phosphate buffer, pH 6.8. A 1.2 μ filter (available from Millipore) is attached to the column, and a 0.2 u filter is attached to the 1.2 u filter. A 22-gauge sterile, nonpyrogenic needle is attached to the 0.2 u filter.

The reaction mixture is drawn up into a 3 mL or 5 mL syringe, and any air bubbles are removed from the solution. After removal of the needle, the syringe is connected to the QAE-Sephadex column on the end opposite the filters. The needle cap is removed from the 22-gauge needle attached to the filter end of the column and the needle tip is inserted into a sterile, nonpyrogenic 10 mL nonevacuated empty vial labeled radio-labeled antibody. Slowly, over 2 minutes, the reaction mixture is injected into the column. The now empty syringe on top of the column is replaced with a 5 mL syringe containing 5 mL of 75 mM (0.45%) sodium chloride solution (from which air bubbles had been removed). Slowly, over 2 minutes, the NaCl solution is injected into the column, and the eluent is collected in the serum vial.

The total radioactivity in the serum vial is measured using a dose calibrator. The yield of the radiolabeled antibody is normally in the 40–60% range. The contents of the serum vial are drawn up into a sterile, pyrogen-free, 30 cc syringe and diluted to a total volume of 30 mL with sterile 0.9% NaCl for injection into a human patient. A quality control test is normally performed on a 0.01 mL aliquot before injection by instant thin layer chromatography.

If the radiochemical purity is less than 85%, the material should not be injected into a human patient. Using this procedure, radiochemical purities generally range from about 90% to 99%. The total amount of radioactivity also is measured prior to injection. In general, from 10 to 30 mCi will be administered to a human patient.

Prior to administering the radiolabeled F(ab) fragment (the diagnostic radiolabeled antibody fragment), an irrelevant antibody and an unlabeled specific antibody are to be administered to the patient to improve the diagnostic images, as described above. The irrelevant antibody, provided in a separate vial in the kit, is a whole murine monoclonal antibody directed against a B-cell lymphoma idiotype. The unlabeled specific antibody, also is in the kit. Both the irrelevant antibody and the unlabeled specific antibody are administered.

The entire 30 mL sample containing the radiolabeled antibody fragment is administered to a patient by intravenous infusion. The infusion is completed in from about 5 min. to about 15 min. The antibody fragment concentration in the sample is 0.33 mg/mL.

2. Post-formed: Technetium-99m labeling of antibody-chelating compound conjugate.

Stannous tartrate kits were prepared from degassed solutions of 0.5 mL disodium tartrate (10 mg/mL) and 0.1 mL stannous chloride (1.0 mg/mL in ethanol) in an evacuated vial under nitrogen atmosphere. To a stannous tartrate kit, sodium pertechnetate 0.5 mL (about 15 mCi) is added and heated at 50° C. for 10–15 min. After cooling to room temperature, quality control for $^{99m}Tc$ tartrate and insoluble $^{99m}Tc$ is carried out on Gelman ITLC using methyl ethyl ketone and 0.01M sodium tartrate pH 7.0 eluents, respectively. $^{99m}Tc$-tartrate formation is typically 98–99% with soluble $^{99m}Tc$ values as $Tco_2$ ranging from 0.1 to 0.2%.

In an evacuated vial, 200 ul of sodium phosphate (0.2M, pH 8.0) and 200 ul of antibody-ligand conjugate (1.9 mg/mL) are added successively. Immediately after adding the conjugate, 250 ul of $^{99m}Tc$-tartrate (about 3 to 5 mCi is added and heated at 37° C. for 1 hour. The percent technetium bound to the protein and the formation of pertechnetate are determined by ITLC using either 12% TCA or 50% MeOH: 10% ammonium acetate (1:1) and 1-butanol eluents, respectively. Technetium incorporation typically ranges from 70–90% on a chelating compound-Ab conjugate with a chelating compound per antibody ratio of 1.5 to 3.0.

B. Therapeutic Kit

1. Pre-formed a. A therapeutic kit containing reagents for preparation of a $^{188}Re$-radiolabeled protein conjugate is as follows.

Sodium perrhenate (3 mL, 15 to 150 mCi, produced from a $^{188}W/^{188}Re$ research scale generator) is added to a vial containing a lyophilized mixture comprising citric acid, 75 mg; stannous chloride, 0.75 mg; gentisic acid, 0.25 mg; and lactose, 75 mg. The vial is agitated gently to mix the contents, then incubated at room temperature for 15 minutes to form a $^{188}Re$-citrate exchange complex. To a separate vial containing 0.50 mg of succinimidyl-bis-4,5-(2',3'-mercaptoisobutyryl)propionamido pentanoate 20 (an $N_2S_4$ chelating agent of the invention comprising isobutyl S-protective groups and a succinimidyl ester group), 0.50 mL of isopropyl alcohol is added and the vial is agitated for 2 min. to completely dissolve the chelating agent. Next, 0.30 mL of this solution is transferred to the vial containing the $^{188}Re$-citrate complex prepared above.

After gentle mixing, the vial is incubated in a 75° C.±2° C. water bath for 15 min., then immediately transferred to a 0° C. ice bath for 2 min. The yields of $^{188}Re$-labeled chelate then range between 75% and 90%.

A column containing a $C_{18}$ reversed phase low-pressure material (Baker $C_{18}$ cartridges) is used to purify the $^{188}Re$-labeled chelate. After conditioning of the cartridge with ethanol and water, the sample is loaded and washed with 2 mL of water three times and 2 mL of 20% ethanol/0.01M phosphate buffer three times. The column is then dried in vacuo and eluted with two times 1.0 mL acetonitrile. About 75% of the $^{188}Re$-radioactivity is normally recovered in greater than 95% purity as the chelate compound.

The chelate is then conjugated to a Fab fragment of a monoclonal antibody directed against an antigen on melanoma cells or small cell lung carcinoma.

A buffered solution of the antibody fragment (5 mg/mL, 0.5 mL) is added to the purified $^{188}Re$-labeled chelate, followed by 0.5 mL of 0.5M carbonate/bicarbonate buffer pH 9.50. The reaction is kept at room temperature for 15 min., then 25 mg of L-lysine, 0.1 mL, is added and the reaction is pursued at room temperature for 15 min. more.

A column containing Sephadex G-25 material is used to purify the $^{188}Re$ conjugate. The reaction mixture is loaded on top of the column, and 1.2 mL aliquots are collected using PBS buffer to rinse the reaction vial and elute the $^{188}Re$ conjugate in the third and fourth fractions. The purity of the $^{188}Re$ conjugate is usually greater than 97% for about 35% overall radiochemical yields. The conjugate is then further diluted with PBS, and radioactivity is measured prior to injection into the test animals and human subjects.

b. A therapeutic kit containing reagents for preparation of a $^{186}Re$-radiolabeled protein conjugate is as follows. The procedure is conducted under conditions which insure the sterility of the product. Proper shielding is used when a radioisotope is introduced.

A target of Re metal (0.1 to 0.25 mg preferentially 0.15 mg) in quartz vial is irradiated for 15 days in the high core of a nuclear reactor with neutraon flux of ca. $5 \times 10^{14}$ neutrons/cm² sec. The target is dissolved with nitric acid and further diluted with sterile water to 5 mL. Upon reception, 0.8 mL of ammonia and 1.0 mL of a tetrabutylanimonium solution were added. The stock solution or aliquot thereoff is loaded on a $C_{18}$ cartridge and washed with water. The Re-186 radioactivity is eluted with 2.0 mL through a sulfonic acid cation exchange column preequilibrated with lithium carbonate solution. The perrhenate solution is dried at 75° C. with a flow of nitrogen. A lyophilized kit comprising 25 mg citric acid, 1 mg stanneous chloride, 1 mg gentisic acid and 75 mg lactose is reconstituted with 1.0 mL of sterile water, and 0.75 mL were removed and added to the dry perrhenate. To a separate vial containing 1.2 mg of succinimidyl-bis-4,5-(2',3'-mercaptoisobutyryl)propionamido pentanoate 20 (or any appropriate ligand), 0.4 mL of isopropylalcohol is added and 0.2 mL is removed and transferred to the vial containing the $^{186}$Re activity. The vial is incubated at 75° C. for 20 min. then cooled to room temperature using an ice water bath. The yields of $^{186}$Re-labeled chelate ranged between 70 and 90%.

The $^{186}$Re solution is passed through two columns; one made of sulfonic acid cation exchange resin; the second made of $C_{18}$ reverse phase material. After water washed and 10% ethanol washes, the $^{186}$Re activity is eluted in another reaction vial with 2.0 mL ethanol. Again, the ethanolic solution is dried at 75° C. and a flow of nitrogen, then equilibrated at room temperature.

The chelate is then conjugated to a F(ab')$_2$ fragment of a monoclonal antibody directed against colon cancer cells. Fifty to 100 mg of antibody fragment (20 mg/mL) is added to the dry $^{186}$Re chelate and 0–5 mL of 1.0M carbonate buffer with 9–9.5 is added. The reaction is kept at room temperature for 15 rain; an aqueous solution of lysine (250 mg kit, 0.1 mL) is added and the reaction continued for 5 more min.

A column containing 15 or 30 cc bed volume of an acrylamide gel for gel permentation is used to purify the $^{186}$Re conjugate. The reaction mixture is loaded on top of the column and 8 mL (in the case of the 15 mL column) or 16 mL (for the 30 mL column) were collected using PBS buffer in a vial containing approximately 1% MSA. The conjugate is diluted to 30 cc with saline and the $^{186}$Re radioactivity is measured prior to injection into test animals and human subjects. The purity of the conjugate is greater than 97% for about 40% overall radiochemical yields.

2. Post-formed a. The $^{188}$Re chelate form of the conjugate is prepared in a procedure similar to that described for $^{99m}$Tc above. Sodium perrhenate (3 mL, 15 mCi, produced from a $^{188}$W/$^{188}$Re generator) is added to a vial containing a lyophilized mixture comprising: citric acid, 75 mg; stannous chloride, 0.75 mg; gentisic acid, 0.25 mg; and lactose, 75 mg. The vial is agitated gently to mix the contents, then incubated at room temperature for 10 min. to form a $^{188}$Re-citrate complex. The reaction mixture is heated at 75° C. for 15 min., then cooled on ice for 5 min. to ready the $^{188}$Re-citrate complex for labeling of the conjugate.

Labeling of the conjugate is carried out in a similar procedure described for Tc above.

b. The $^{186}$Re chelate form of the conjugate is prepared in a procedure similar to that described in the Pre-formed procedure.

EXAMPLE V

Biodistribution Studies in Mice

A. With $^{99m}$Tc-labeled Monoclonal Antibody Fragment

Antibody fragments radiolabeled with $^{99m}$Tc according to the procedures outlined in Examples II and III are injected into mice. The biodistribution of the radionuclide protein conjugate is analyzed for 20 hours after injection according to the method of Hwang et al., *Cancer Res.*, 45: 4150–4155 (1985). The antibody fragment is a Fab fragment of the above-described monoclonal antibodies: NR-ML-05, NR-LU-10, NR-CO-02, NR-Ce-01. The data is collected in terms of the percentage of the injected radioactivity per gram of each specified tissue type and tumor/tissue ratio of injected radioactivity. The tissue types evaluated are as follows: tail; tumor, skin; muscle; bone; lung; liver; spleen; stomach; thyroid; kidney; and intestine. Tumor sites effectively identified in each of the mice.

B. With $^{188}$Re-labeled Monoclonal Antibody Fragment

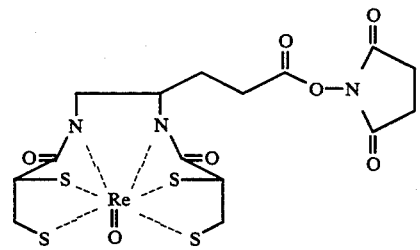

The chelate Re-N$_2$S$_4$, in which the radionuclide metal is $^{188}$Rhenium as shown above, is prepared by the methods described herein. The chelate is conjugated to a Fab fragment of a monoclonal antibody specific for a tumor, e.g., NR-ML-05, NR-LU-10, NR-CO-2, or NR-Ce-1. The Fab fragment is produced by treatment of the monoclonal antibody with papain according to conventional techniques. The conjugation step and purification of the resulting radiolabeled antibody are as described in Example II. The chelate-antibody conjugate is injected into tumor-bearing mice, biodistribution of the radiolabeled material is analyzed 20 hours after injection according to the method of Hwang et al., *Cancer Res.* 45: 4150–4155, 1985, and compared to Tc-99m biodistribution.

C. With $^{186}$Re-Labeled Monoclonal Antibody Fragment

The chelate Re-N$_2$S$_4$ in which the radionuclide method is $^{186}$Re is prepared by the methods described herein. To verify tumor uptake, the chelate is conjugated to a Fab fragment of NRMI or antibody. The chelate-antibody conjugate is injected into tumor-bearing mice, biodistribution is analyzed after 20 hours and compared to Re-199 biodistribution.

EXAMPLE VI

Imaging of Tumors in Humans

Antibody fragments radiolabeled with $^{99m}$Tc according to the method of the invention are injected into human patients to detect tumor sites, i.e., melanoma, lung, colon) within the body. The antibody fragments used are F(ab)$_2$, Fab' or Fab fragments of monoclonal antibodies specific for an antigen of the particular tumor. The antibody fragment used may be, for example, a fragment of a monoclonal antibody designated NR-ML-05, NR-LU-10, NR-CE-01 or NR-CO-02, described above. The fragments are generated by standard techniques (i.e., pepsin treatment of the monoclonal antibody to generate the F(ab')$_2$ fragment, papain treatment of the monoclonal antibody to generate the Fab fragment, and treatment with a reducing agent such as dithiothreitol or cysteine to generate the Fab' fragment).

The chelate compound (Tc-N$_2$S$_4$):

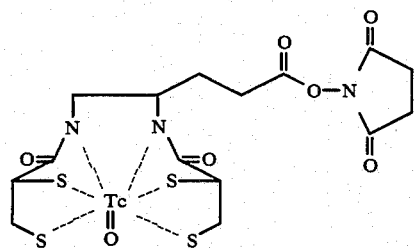

is prepared by one of the methods described herein. A patient receives the chelate prepared and conjugated to the antibody fragment according to the procedures outlined in Examples II and III. The resulting radiolabeled antibody fragment is purified, and a quality control test is performed, as described in Example III. Approximately 40 min. to 1 hour and 30 min. prior to infusion of the radiolabeled antibody, each patient may receive 41 to 50 mg of an irrelevant antibody in 12 to 20 mL of sterile saline by intravenous infusion. In addition, each patient receives 7.5 mg of a non-radiolabeled specific antibody in 20 mL of sterile saline by intravenous infusion either simultaneously with, or approximately 5 min. prior to infusion of the radiolabeled specific antibody. The non-radiolabeled specific antibody is exactly the same as the one used for radiolabeling. The irrelevant antibody is a monoclonal antibody designated NR2AD, which is a murine $IgG_{2a}$ immunoglobulin that is designed as an anti-idiotype that bound to a single patient's B-cell lymphoma and to no other human tissue.

Into each patient is injected 20 to 30 mL of sterile saline comprising the radiolabeled antibody fragment, by intravenous infusion. The patients receive from 10 mCi to about 30 mCi of $^{99m}Tc$ radioisotope. The desired upper limit of radioisotope administered is 30 mCi, and the minimum for effective imaging of tumors is generally about 10 mCi. The total amount of protein in the administered solutions ranged from 2.5 mg to 1.0 mg. Imaging with a gamma camera is performed at three time points: immediately following infusion, from 7 to 8 hours post infusion, and from 19 to 20 hours post infusion. The best images of the target sites (tumors) are achieved by imaging at from 7 to 8 hours after completion of infusion of the radiolabeled antibody. Although some accumulation of radioactivity in the kidneys is detected during these imaging procedures, the kidneys generally are not considered to be target sites in the diagnostic procedures of the invention. The percentage of the total injected dose radioactivity (in cpm) which had localized in each of the various tissue types sampled are to be calculated. The ratio of the radioactivity found in tumor site(s) to the radioactivity found in the other types of tissue are also calculated. The value for the percent injected dose per mg for the tumor tissue in a particular patient is divided by the value for the percent injected dose per mg for each non-tumor tissue sample biopsied from the patient to give the tumor:tissue ratio for each non-tumor tissue sample.

From the foregoing, it will be appreciated that, although specific embodiments of the invention have been described herein for purposes of illustration, various modifications may be made without deviating from the spirit and scope of the invention.

We claim:

1. A compound having the formula:

wherein:

$X_1$ and $X_2$ are H or =O, but both are not =O;
$X_3$ and $X_4$ are H or =O, but both are not =O;
A is H, alkyl group of $C_6$ or less, $-CH_2-CH_2-S-R_1$, or $-CO-CH_2-S-R_1$, with the proviso that when $X_1$ or $X_2$ is =O, A is H;
A' is H, alkyl group of $C_6$ or less, $-CH_2-CH_2-S-R_2$, or $-CO-CH_2-S-R_2$, with the proviso that when $X_3$ or $X_4$ is =O, A' is H;
Y is
 (a) $-CH_2-S-R_3$, or H, when A is H or an alkyl group of $C_6$ or less and A' is H or an alkyl group of $C_6$ or less, or
 (b) H, with the proviso that Y must be selected from (a) when A is H or an alkyl group of $C_6$ or less and A' is H or an alkyl group of $C_6$ or less;
Y' is
 (a) $-CH_2-S-R_4$, or H, when A is H or an alkyl group of $C_6$ or less and A' is H or an alkyl group of $C_6$ or less, with the proviso that Y and Y' are not both H, or
 (b) H, with the proviso that Y' must be selected from (a) when A is H or an alkyl group of $C_6$ or less and A' is H or an alkyl group of $C_6$ or less;
$R_1$, $R_2$, $R_3$, $R_4$, $R_5$, and $R_6$ are independently selected from sulfur protecting groups;
Q is H or a polar group;
n is 0 to 2; and
Z is $-(W)_m-R'$, where W is $-CH_2-$, $-CH_2-O-$, $-CH_2-CO-$, or combinations thereof, m is 0 to 5, and R' is a conjugation group, with the provisos that when Z is attached to the carbon designated α there is either no $X_1$ or no Q at α, that when Z is attached to the carbon designated β there is either no $X_3$ or no Q at β, that when $X_1$ is =O there is no Z at α, and that when $X_3$ is =O there is no Z at β.

2. The compound of claim 1 wherein said compound has the formula:

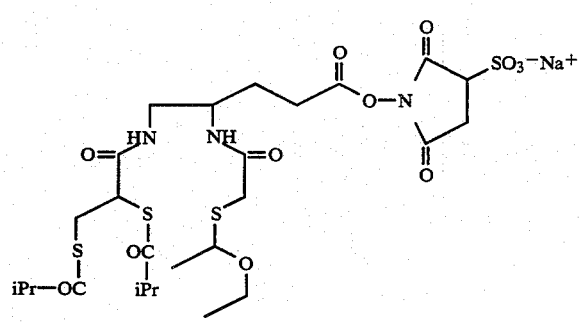

3. The compound of claim 1 wherein said compound has the formula:

4. The compound of claim 1 wherein said compound has the formula:
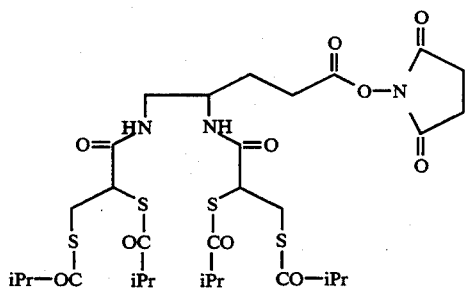
5. The compound of claim 1 wherein said compound has the formula:
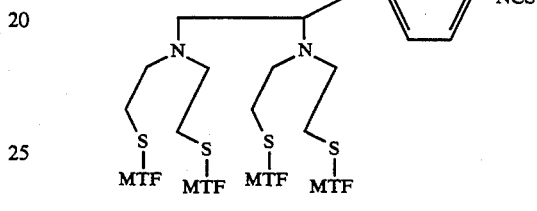
* * * * *

UNITED STATES PATENT AND TRADEMARK OFFICE
CERTIFICATE OF CORRECTION

PATENT NO. : 5,436,352
DATED : July 25, 1995
INVENTOR(S) : Ananthachari Srinivasan, Alan R. Fritzberg and David S. Jones It is certified that error appears in the above-indentified patent and that said Letters Patent is hereby corrected as shown below:

In column 44, claim 2, underneath the chemical structure, please insert -- wherein iPr is isopropyl --.

In column 45, claim 3, underneath the chemical structure, please insert -- wherein iPr is isopropyl --.

In column 46, claim 4, underneath the chemical structure, please insert -- wherein iPr is isopropyl --.

Signed and Sealed this

Twenty-third Day of January, 1996

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,436,352
DATED : July 25, 1995
INVENTOR(S) : Ananthachari Srinivasan, Alan R. Fritzberg and David S. Jones It is certified that error appears in the above-indentified patent and that said Letters Patent is hereby corrected as shown below:

Column 1, line 56, delete the extra period "." after "fragments.".

Column 2, line 34, after "less,", delete "3".

Column 5, line 40, delete "hemithioacetai" and insert -- hemithioacetal --.

Column 5, line 46, delete "sulfydryls and insert -- sulfhydryls --.

Column 8, line 55, between "capable" and "being", insert -- of --.

Column 8, line 56, insert a period -- . -- after "conjugate".

Column 10, line 42, delete "integer,s" and insert -- integers --.

Column 12, line 6, between "agent" and "will", insert -- . It --.

Column 14, line 24, delete the semicolon ";" before "effective".

Column 18, line 10, delete "succimimidate" and insert -- succinimidate --.

Column 18, line 23, delete the period "." between "in" and "125".

Column 18, line 43, delete "MgSo$_4$" and insert -- MgSO$_4$ --.

Column 18, line 48, delete "either" and insert -- ether --.

UNITED STATES PATENT AND TRADEMARK OFFICE
CERTIFICATE OF CORRECTION

PATENT NO. : 5,436,352
DATED : July 25, 1995
INVENTOR(S) : Ananthachari Srinivasan, Alan R. Fritzberg and David S. Jones It is certified that error appears in the above-indentified patent and that said Letters Patent is hereby corrected as shown below:

Column 19, line 54, delete "N-Benyloxycarbonyl" and insert -- N-Benzyloxycarbonyl --.

Column 19, line 55, delete "N- Benyloxycarbonyl" and insert -- N-Benzyloxycarbonyl --.

Column 19, line 58, delete "N-Benyloxy-carbonyl-" and insert -- N-Benzyloxycarbonyl- --.

Column 19, line 63, between "addition" and "ether", delete "I" and insert -- of --.

Column 19, line 64, delete "N- Benyloxycarbonyl" and insert -- N-Benzyloxycarbonyl --.

Column 20, line 21, delete "diminopentanoic" and insert -- diaminopentanoic --.

Column 20, line 26, delete "mercaptioisobuyryl" and insert -- mercaptoisobutyryl --.

Column 22, line 25, delete "diminopentanoic" and insert -- diaminopentanoic --.

Column 26, in the lower left substituent in chemical structure 39, delete "TSE" and insert -- TMSE --.

Column 27, line 64, delete "diaminopropul" and insert -- diaminopropyl --.

Column 27, line 66, delete "floride" and insert -- fluoride --.

UNITED STATES PATENT AND TRADEMARK OFFICE
CERTIFICATE OF CORRECTION

PATENT NO. : 5,436,352
DATED : July 25, 1995
INVENTOR(S) : Ananthachari Srinivasan, Alan R. Fritzberg and David S. Jones It is certified that error appears in the above-indentified patent and that said Letters Patent is hereby corrected as shown below:

Column 28, line 14, delete "S-isobutryl" and insert -- S-isobutyryl --.

Column 28, line 19, delete the extra period "." after "2".

Column 28, line 28, delete "isobutrylmercaptoacetic" and insert -- isobutyrylmercaptoacetic --.

Column 28, line 28, delete "1H" and insert -$^{1}$H --.

Column 29, lines 10-17, delete

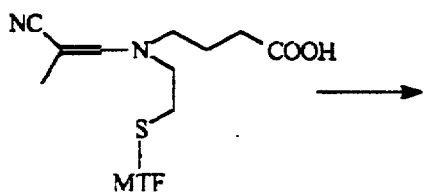

and insert the structure below:

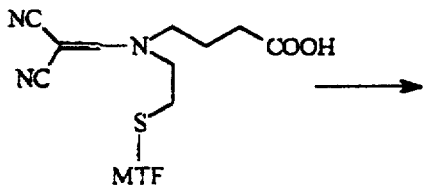

45

UNITED STATES PATENT AND TRADEMARK OFFICE
CERTIFICATE OF CORRECTION

PATENT NO. : 5,436,352
DATED : July 25, 1995
INVENTOR(S) : Ananthachari Srinivasan, Alan R. Fritzberg and David S. Jones It is certified that error appears in the above-indentified patent and that said Letters Patent is hereby corrected as shown below:

Column 29, lines 18-24, delete

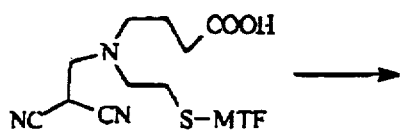

and insert the structure below:

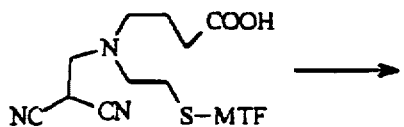

46

Column 30, line 11, delete "N-β,β-Dicyano)" and insert -- N-(β,β-Dicyano) --.

Column 30, line 24, delete "N-β,β-Diaminomethyl" and insert -- N-(β,β-Diaminomethyl --.

Column 30, line 63, between "residue" and "is", delete "in".

Column 30, line 53, delete "mercarap" and insert -- mercap --.

Column 33, line 27, delete "glove" and insert -- give --.

UNITED STATES PATENT AND TRADEMARK OFFICE
CERTIFICATE OF CORRECTION

PATENT NO. : 5,436,352
DATED : July 25, 1995
INVENTOR(S) : Ananthachari Srinivasan, Alan R. Fritzberg and David S. Jones It is certified that error appears in the above-indentified patent and that said Letters Patent is hereby corrected as shown below:

Column 34, line 16, delete "bury" and insert -- buty --.

Column 34, line 25, delete "captoactamido" and insert -- captoacetamido --.

Column 34, line 28, delete "S-isobutrylmercaptoacetic" and insert -- S-isobutyrylmercaptoacetic --.

Column 34, line 36, delete "toactamido" and insert -- toacetamido --.

Column 34, line 44, delete "either" and insert -- ether --.

Column 35, line 56, delete "Bernlet" and insert -- Bernier --.

Column 36, line 6, delete "Asceptic" and insert -- Aseptic --.

Column 36, line 24, delete "supernatent" and insert -- supernatant --.

Column 37, line 7, delete "conugate" and insert -- conjugate --.

Column 37, line 15, delete "field" and insert -- yield --.

Column 40, line 55, delete "neutraon" and insert -- neutron --.

Column 40, line 59, delete "tetrabutylanimonium" and insert -- tetrabutylammonium --.

Column 41, line 20, delete "0-5" and insert -- 0.5 --.

UNITED STATES PATENT AND TRADEMARK OFFICE
CERTIFICATE OF CORRECTION

PATENT NO. : 5,436,352
DATED : July 25, 1995
INVENTOR(S) : Ananthachari Srinivasan, Alan R. Fritzberg and David S. Jones It is certified that error appears in the above-indentified patent and that said Letters Patent is hereby corrected as shown below:

Column 41, line 22, delete "rain" and insert -- min --.

Column 41, line 26, delete "permentation" and insert -- permeation --.

Column 43, line 41, delete "1.0" and insert -- 10 --.

Signed and Sealed this

Twenty-ninth Day of October 1996

Attest:

BRUCE LEHMAN

Attesting Officer

Commissioner of Patents and Trademarks